(12) United States Patent
Nogaret et al.

(10) Patent No.: US 12,128,238 B2
(45) Date of Patent: Oct. 29, 2024

(54) PACEMAKER DEVICE

(71) Applicant: CERYX MEDICAL LIMITED, Wales (GB)

(72) Inventors: Alain Nogaret, Wales (GB); Julian Paton, Wales (GB); Paul Curzons, Wales (GB); Ashok Singh Chauhan, Wales (GB)

(73) Assignee: CERYX MEDICAL LIMITED, Wales (GB)

( * ) Notice: Subject to any disclaimer, the term of this patent is extended or adjusted under 35 U.S.C. 154(b) by 138 days.

(21) Appl. No.: 17/641,753

(22) PCT Filed: Sep. 8, 2020

(86) PCT No.: PCT/GB2020/052149
§ 371 (c)(1),
(2) Date: Mar. 9, 2022

(87) PCT Pub. No.: WO2021/048530
PCT Pub. Date: Mar. 18, 2021

(65) Prior Publication Data
US 2022/0314004 A1   Oct. 6, 2022

(30) Foreign Application Priority Data

Sep. 10, 2019 (GB) .................................... 1913050

(51) Int. Cl.
*A61N 1/36* (2006.01)
*A61N 1/365* (2006.01)

(52) U.S. Cl.
CPC ............................. *A61N 1/36514* (2013.01)

(58) Field of Classification Search
CPC ............................. A61N 1/36514; A61N 1/365
See application file for complete search history.

(56) References Cited

U.S. PATENT DOCUMENTS

| 3,593,718 A | 7/1971 | Krasner et al. |
| 4,567,892 A | 2/1986 | Plicchi et al. |

(Continued)

FOREIGN PATENT DOCUMENTS

| JP | 2010-531164 A | 9/2010 |
| JP | 2018-508299 A | 3/2018 |

(Continued)

OTHER PUBLICATIONS

Bristol Heart Institute, "Novel pacemaker technology could transform treatment of heart failure," University of Bristol, 2017.

(Continued)

*Primary Examiner* — Rex R Holmes
(74) *Attorney, Agent, or Firm* — Perkins Coie LLP

(57) ABSTRACT

The disclosure relates to determining timing of electrical stimulus signals temporally modulated by a respiration signal. Aspects of the disclosure relate to an apparatus comprising: a first input stage configured to receive a first input signal indicative of respiration; a respiration analysis module configured to determine, from the first input signal, a signal indicative of instantaneous respiration duty cycle; and a synchronization module configured to generate the timing of the stimulus signals as a function of the signal indicative of respiration duty cycle in order to maintain a bias towards synchronization between the respiration period and an integer ratio of the periods between stimulus signals.

18 Claims, 18 Drawing Sheets

(56) References Cited

U.S. PATENT DOCUMENTS

| | | | |
|---|---|---|---|
| 4,576,183 A | 3/1986 | Plicchi et al. | |
| 4,596,251 A | 6/1986 | Plicchi et al. | |
| 4,930,518 A | 6/1990 | Hrushesky | |
| 5,690,688 A | 11/1997 | Noren et al. | |
| 5,964,788 A | 10/1999 | Greenhut | |
| 6,141,590 A | 10/2000 | Renirie et al. | |
| 6,165,134 A | 12/2000 | Marchesi | |
| 6,208,900 B1 | 3/2001 | Ecker et al. | |
| 6,305,943 B1 | 10/2001 | Pougatchev et al. | |
| 6,487,442 B1 | 11/2002 | Wood | |
| 7,231,250 B2 | 6/2007 | Band et al. | |
| 7,302,295 B2 | 11/2007 | Stahmann et al. | |
| 7,539,539 B1 | 5/2009 | Bharmi | |
| 8,005,543 B2 | 8/2011 | Libbus et al. | |
| 8,075,491 B2 | 12/2011 | Bharmi | |
| 8,265,753 B2 | 9/2012 | Higham et al. | |
| 8,478,389 B1* | 7/2013 | Brockway | A61B 5/349 600/509 |
| 8,483,833 B2 | 7/2013 | Cho et al. | |
| 8,620,427 B2 | 12/2013 | Libbus et al. | |
| 9,563,839 B2 | 2/2017 | Nogaret | |
| 10,893,813 B2 | 1/2021 | Libbus et al. | |
| 2009/0024176 A1 | 1/2009 | Yun et al. | |
| 2015/0178618 A1* | 6/2015 | Nogaret | G06N 3/04 706/26 |
| 2016/0110643 A1* | 4/2016 | Basu | G06F 17/16 706/22 |
| 2017/0056669 A1* | 3/2017 | Kane | A61N 1/36521 |
| 2018/0117316 A1* | 5/2018 | Wagner | A61B 5/686 |
| 2018/0192941 A1* | 7/2018 | Annoni | A61N 1/37264 |

FOREIGN PATENT DOCUMENTS

| | | |
|---|---|---|
| WO | 9602185 A1 | 2/1996 |
| WO | 03077991 A1 | 9/2003 |
| WO | 2012154706 A1 | 11/2012 |
| WO | 2013175171 A2 | 11/2013 |

OTHER PUBLICATIONS

Donati, Elisa, et al., "Deriving optimal silicon neuron circuit specifications using Data Assimilation," In 2018 IEEE International Symposium on Circuits and Systems. IEEE, ISCAS 2018, Jan. 3, 2018.

Nogaret, Alain, et al., "Silicon central pattern generators for cardiac diseases", Topical review, J Physiol 593.4 (2015) pp. 763-774.

Examination Report mailed Mar. 23, 2023 for Patent Application No. GB1913050.9 (3 pages).

Intention to Grant mailed Jul. 5, 2023 for Patent Application No. GB1913050.9 (2 pages).

Response to Examination Report for UK Patent Application No. 1913050.9 filed Apr. 25, 2023 (6 pages).

Response to Search Report filed Sep. 2, 2021 for UK Patent Application No. 1913050.9 (2 pages).

Search Report mailed Feb. 6, 2020 for Application No. GB1913050.9 (2 pages).

International Search Report and Written Opinion mailed Dec. 11, 2020 for International Patent Application No. PCT/GB2020/052149.

O'Callaghan, Erin L., et al. "Utility of a Novel Biofeedback Device for Within Breath Modulation of Heart Rate in Rats: A Quantitative Comparison of Vagus Nerve vs. Right Atrial Pacing," Frontiers in Physiology vol. 7, Art. 27, 2016.

C. P. Lau et al, "Rate-Responsive Pacing with a Pacemaker That Detects Respiratory Rate (Biorate) : Clinical Advantages and Complications", Clin. Cardiol. 11, 318-324 (1988).

H. Krause, "On the difference of cardiorespiratory synchronisation and coordination", Chaos 27, 093933 (2017); https://doi.org/10.1063/1.4999352.

M. Elstad et al., "Cardiorespiratory interactions in humans and animals: rhythms for life" Am J Physiol Heart Circ Physiol. Jul. 1, 2018;315(1): H6-H17. doi: 10.1152/ajpheart.00701.2017. Epub Mar. 9, 2018.

Schafer, Carsten, et al., "Synchronization in the human cardiorespiratory system," The American Physical Society, Physical Review E, vol. 60, No. 1, Jul. 1999, pp. 857-870.

Decision to Grant from Japanese Patent Application No. 2022-515669 dated Jul. 16, 2024.

* cited by examiner

HR/RR=1, $I_{exp}$ = 0.7nA $I_{insp}$ varies

HR/RR=2, $I_{exp}$ = 0.7nA $I_{insp}$ varies

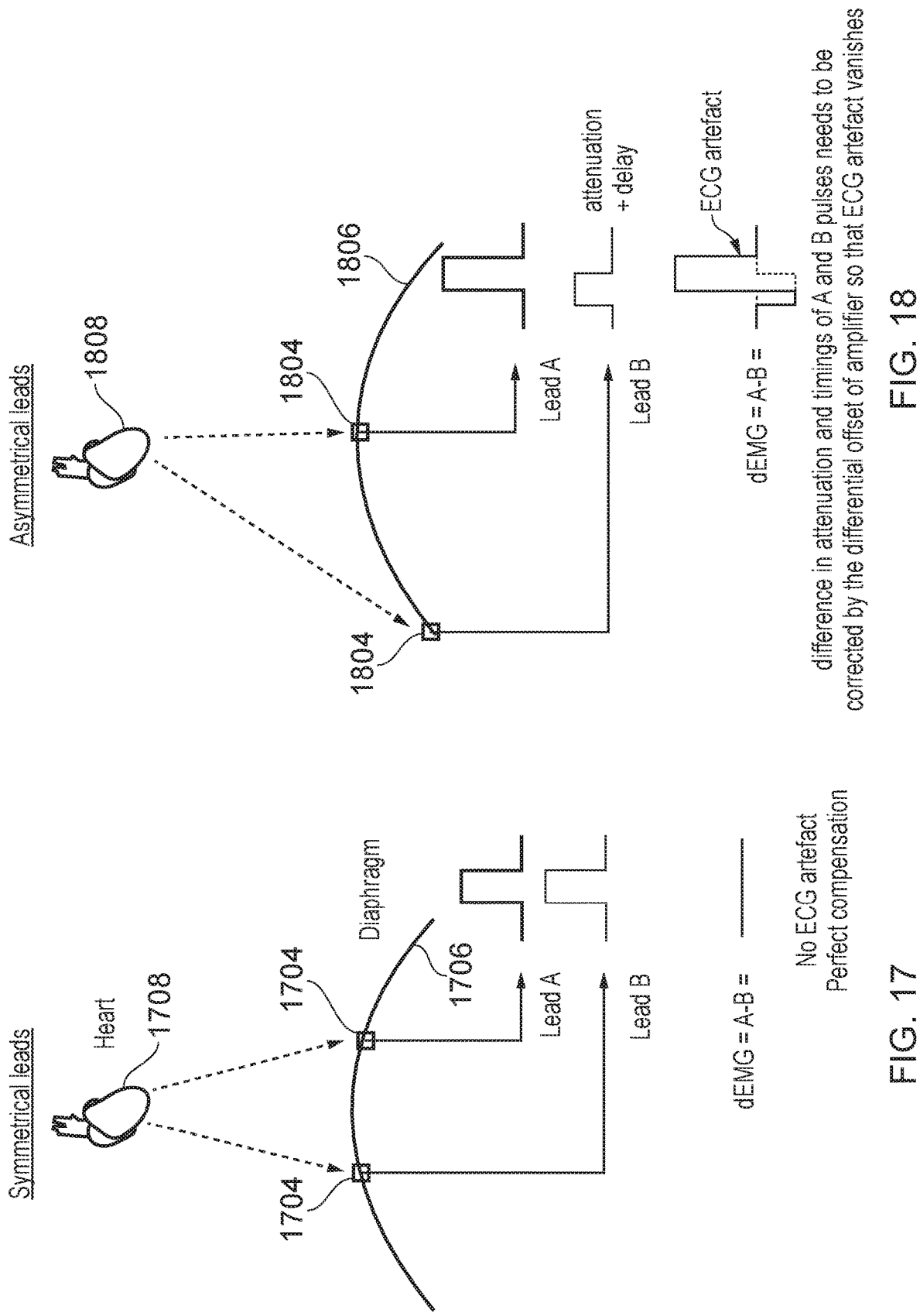

Spike with 8% positive offset applied to trace 2 input signal

Spike with 8% positive offset applied to trace 2 input signal, but partially equalised Spike with 8% positive offset applied to trace 2 input signal, but equalised

PACEMAKER DEVICE

This patent document is a 371 National Phase Application of International Patent Application No PCT/GB2020/052149, filed Sep. 8, 2020, which claims priority to the United Kingdom Patent Application No. 1913050.9, filed Sep. 10, 2019. The entire contents of the above-referenced applications are incorporated by reference as part of the disclosure of this document.

The invention relates to the field of cardiac pacemaker devices, and in particular, although not exclusively, to cardiac pacemaker devices that are configured to provide a respiratory sinus arrhythmia.

Cardiac pacemaker devices may be used to stimulate atrial activity in a subject in which the normal biological systems for stimulating such activity have failed.

According to a first aspect there is provided an apparatus for determining timing of electrical stimulus signals temporally modulated by a respiration signal, comprising:
- a first input stage configured to receive a first input signal indicative of respiration;
- a respiration analysis module configured to determine, from the first input signal, a signal indicative of instantaneous respiration duty cycle; and
- a synchronization module configured to generate the timing of the stimulus signals as a function of the signal indicative of respiration duty cycle in order to maintain a bias towards synchronization between the respiration period and an integer ratio, or integer multiple, of the periods between stimulus signals, which may also be referred to as stimulus signal periods.

The electrical stimulus signals may be cyclical electrical stimulus signals. The integer multiple of the stimulus signal periods may be a predetermined number.

The synchronization module may modulate the timing of the stimulus signals according to a non-linear function. The synchronization module may comprise a neuronal oscillator.

The synchronization module may comprise a neuronal oscillator. The timing of the stimulus signals may comprise modulating a base frequency for the heart. The neuronal oscillator may comprise a single neuronal oscillator. That is, the neuronal oscillator may comprise only one neuron or a system emulating only one neuron.

The apparatus may further include a non-linear oscillator. The non-linear oscillator may be configured to receive a second input indicative of the base frequency for the heart, for example, the current stimulation $I_{exp}$ that determines $f_{exp}$, and the signal indicative of respiration duty cycle. The non-linear oscillator may synchronize to the signal indicative of respiration duty cycle. The current $I_{exp}$ may be set, by a clinician for example, to provide either a fixed heart rate or made to vary with the respiration rate according to a set calibration curve. In the latter, an averaged respiration rate, which may be averaged over the last 5 respiration cycles for example, may be used as a measure of physical activity. The respiration rate may be read by a frequency counter receiving the $I_{inj}$ signal output by 1410 (which may take values of $I_{insp}$ or $I_{iexp}$ during the inspiratory and expiratory phases respectively), discussed below with reference to FIG. 14 (see also FIG. 8*a*, 9*a*, 10*a*) and a digital or analogue amplifier that generates a current proportional to this average frequency.

The respiration duty cycle may have an inspiration phase. The respiration duty cycle may have an expiration phase. The apparatus may further include means for setting a parameter (for example, RSA or (finsp−fexp)/fexp) determining a differential stimulus signal rate between the inspiration and expiration phases.

Each of the periods between stimulus signals within a single inspiration phase or expiration phase may have the same target duration. Each of the stimulus signal periods within a single inspiration phase or expiration phase are intended to be of the same duration but may depart from this state by small deviation to maintain synchronization to respiration.

Maintaining a bias towards synchronization between the respiration period and an integer ratio, or integer multiple, of the periods between stimulus signals may comprise setting a period for the periods between stimulus signals in the inspiration phase or expiration phase.

The synchronization module may be configured to maintain a bias towards synchronization between the inspiration phase or expiration phase of the respiration period and an integer ratio, or integer multiple, of the periods between stimulus signals.

A different integer number of periods between stimulus signals may be provided in the inspiration phase and the expiration phase.

The apparatus may further including means for setting a strength of coupling factor. Said means may determine (i) a speed of synchronization between the non-linear oscillator and the respiration duty cycle signal and/or (ii) a tolerance to frequency mismatch between the respiration period and one or more target heart beat intervals.

The apparatus may comprise an analogue electronic signal processing chain. The electronic signal processing chain may provide the respiration analysis module. The electronic signal processing chain may provide the synchronization module.

The apparatus may comprise a blanking module. The blanking module may be configured to provide a blanking period in the first input signal indicative of respiration based on i) the timing of the stimulus signals or ii) based on detection of stimulus signal interference in the first input signal.

The analysis module may be optically coupled to the synchronization module. The first input signal indicative of respiration may be a dEMG signal or a chest electrical impedance signal. The respiration analysis module may comprise one or more amplifiers. The one or more amplifiers may be configured to amplify the first input signal. The synchronization module may be galvanically isolated from the analysis module. The synchronization module may be galvanically isolated from the one or more amplifiers. The neuronal oscillator may be galvanically isolated from the one or more amplifiers. The neuronal oscillator may be optically coupled to the one or more amplifiers.

According to a further aspect there is provided a system comprising:
- a cardiac pacemaker device comprising an apparatus described herein;
- one or more sensors coupled to the first input stage of the cardiac pacemaker device; and
- pacing electrodes coupled to the cardiac pacemaker device and arranged to receive, from the cardiac pacemaker device, periodic electrical stimulus signals based on the timing information determined by the cardiac pacemaker device.

According to a further aspect there is provided a method for determining timing of electrical stimulus signals temporally modulated by a respiration signal. The method may comprise:

receiving a first input signal indicative of respiration;

determining, from the first input signal, a signal indicative of instantaneous respiration duty cycle; and generating the timing of the stimulus signals as a function of the signal indicative of respiration duty cycle in order to maintain a bias towards synchronization between the respiration period and an integer ratio, or integer multiple, of the periods between stimulus signals. The method may be computer-implemented.

According to a further aspect there is provided a non-transitory computer-readable storage medium comprising computer program code configured to cause a processor to execute a method for determining timing of periodic electrical stimulus signals temporally modulated by a respiration signal.

BRIEF DESCRIPTION OF FIGURES

Embodiments of the present invention will now be described by way of example and with reference to the accompanying drawings in which:

FIG. 17 illustrates an example in which dEMG sensors provided on a diaphragm of a subject and are equally spaced from a heart of the subject;

FIG. 18 illustrates an example in which dEMG sensors provided on a diaphragm 1806 of a subject and are offset with respect to a heart of the subject;

DESCRIPTION OF EXAMPLES

The body's natural regulation of heartbeat is in phase with breathing or respiratory cycle. For example, the heart slows down during expiration (breathing out) and speeds up during inspiration (breathing in). This is referred to as respiratory sinus arrhythmia (RSA). The loss of RSA is a predictor of cardiovascular risk and a prognostic indicator for multiple diseases including heart failure.

In various examples in the present disclosure, a pacing system is provided in order to artificially restore RSA. Such systems aim to slow down disease progression, reverse damage to heart muscle (remodelling of the myocardium), or obtaining better cardiac pumping function from the remaining viable cardiac muscle in order to improve quality of life outcomes for the subject of the cardiac device.

Figure 1:
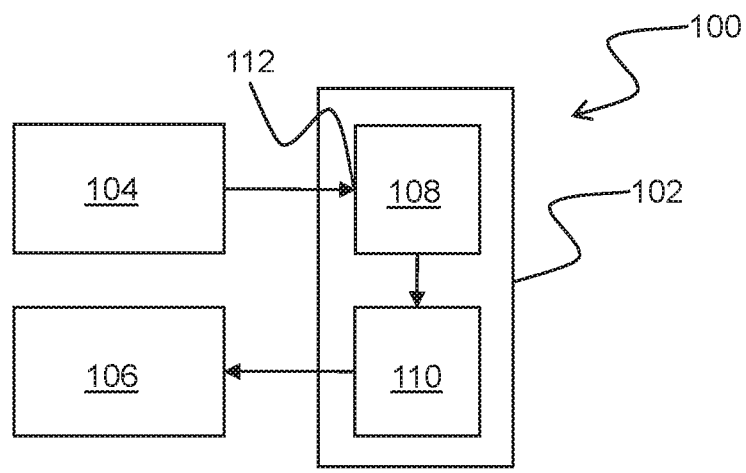
FIG. 1 illustrates a schematic block diagram of a cardiac pacemaker system.

FIG. 1 illustrates a schematic block diagram of a cardiac pacemaker system 100. The cardiac pacemaker system 100 comprises a cardiac pacemaker device 102, one or more sensors 104 and one or more pacing electrodes 106. The pacing system 100 is an electronic device for mimicking the biological RSA control process present in a healthy individual and artificially mimicking it in a subject, which may also be referred to as a patient. The provision of such devices may also prove advantageous, where some RSA still occurs naturally in the patient, to apply RSA at higher levels than naturally occurring using such a device.

The one or more sensors 104 may comprise an electromyography sensor or a chest impedance sensor, for example. Such sensors may be provided by conventional sensors used in the art and may include mechanisms or adhesives for coupling the one or more sensors 104 to the subject. The one or more sensors are configured to sense a signal indicative of respiration of the subject. The cardiac pacemaker device 102 may be configured to communicate with the one or more sensors 104 via a wireless or wired communications link. For example, a near-field communications link could operate through tissue of the patient so that one of i) the cardiac pacemaker device 102 and ii) the one or more sensors 104 is provided internally and the other is provided externally.

The one or more pacing electrodes 106 may be provided by conventional pacing electrodes that are configured to apply an electrical stimulus to the subject. The one or more pacing electrodes 106 may comprise a mechanism or adhesive for attaching the one or more pacing electrodes 106 to the subject.

The cardiac pacemaker device 102 comprises a signal processing unit 108 and an electrical stimulus generator 110. The signal processing unit 108 is configured to receive the signal indicative of respiration of the subject from the one or more sensors 104 at a sensor signal input 112. The signal processing unit is configured to generate timing information for multiple stimuli based on the signal indicative of respiration.

The cardiac pacemaker device 102 may be an implantable device. For example, the cardiac pacemaker device 102 may have a housing, which may be biologically inactive, or non-reactive. The housing may have dimensions of 10 cm or less by 5 cm or less, for example. The cardiac pacemaker device 102 may include a power source to power the device 102.

The electrical stimulus generator 110 is configured to generate the electrical stimulus signals based on the timing information provided by the signal processing unit 108. The electrical stimulus generator 110 may be provided by conventional pulse generation hardware, for example, and is configured to provide the electrical stimulus signals to the one or more pacing electrodes 106.

The signal processing unit 108 may be provided by hardware, software or a combination of hardware and software. In one example, the signal processing unit 108 comprises a respiration analysis module and a synchronisation module. Such modules may be provided as software modules that are executed by hardware, for example.

Figure 2:
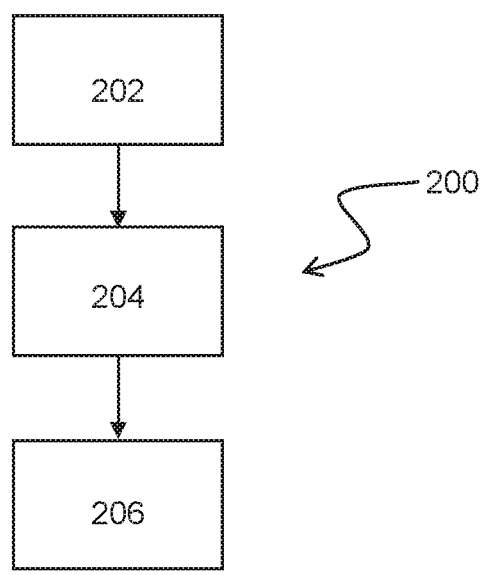
FIG. 2 illustrates a method for determining periodic electrical stimulus signals temporarily modulated by a respiration signal.

FIG. 2 illustrates a method 200 for determining periodic or cyclical electrical stimulus signals temporarily modulated by a respiration signal, which may be performed by the signal processing module described previously with reference to FIG. 1.

The method 200 for determining timing of cyclical electrical stimulus signals temporally modulated by a respiration signal, comprising:
  receiving 202 a first input signal indicative of respiration;
  determining 204, from the first input signal, a signal indicative of an instantaneous respiration duty cycle; and
  generating 206 the timing of the stimulus signals as a function of the signal indicative of the instantaneous respiration duty cycle in order to maintain a bias towards synchronization between the respiration period and an integer ratio of the periods between stimulus signals, which may also be referred to as an inter-stimulus interval or inter-spike intervals.

The use of the first input signal indicative of respiration to control the generation of the timing of the stimulus signals means that the method 200 provides direct physiological feedback. In some examples, the timing of the stimulus signals is generated according to a non-linear function which may be provided by, for example, a neuronal oscillator. The neuronal oscillator may be provided by analogue circuitry implementing, for example, a Central Pattern Generator, or by a digital simulation. There may be provided a computer program, which when run on a computer, causes the computer to configure any apparatus, including a circuit, unit, controller, device or system disclosed herein to perform any method disclosed herein. The computer program may be a software implementation. The computer may comprise appropriate hardware, including one or more processors and memory that are configured to perform the method defined by the computer program.

The computer program may be provided on a computer readable medium, which may be a physical computer readable medium such as a disc or a memory device, or may be embodied as a transient signal. Such a transient signal may be a network download, including an internet download. The computer readable medium may be a computer readable storage medium or non-transitory computer readable medium.

The present inventors recognize that there is an 'energy saving' argument why RSA pacing using a system such as those described with reference to FIG. 1 using a method such as that described with reference to FIG. 2 leads to improved cardiac pumping efficiency.

RSA enables stability of blood gases and in particular carbon dioxide ($CO_2$); a major stimulant of breathing. RSA may enable the heart to save energy because maintaining $CO_2$ can occur with fewer heart beats relative to when monotonic beating occurs. Deep slow breathing increased RSA (and energy saved) but deep slow breathing without RSA neither saved energy nor controlled $CO_2$. The amount of cardiac energy saved by RSA is an ongoing research area. Initial calculations indicate a 3% saving of energy over one breath or 35 calories per hour. Within 3 days this equates to approximately a days' caloric intake.

The present inventors consider that a non-linear synchronisation process between the pulsed heart and lungs of the subject may improve RSA stability compared to linear approaches. Typically, in physics, a synchronised system will result in the lowest energy dissipation. For example, if the coupling between two harmonic oscillators is linear (e.g. a spring) the pushes and the pulls of each oscillator on the other will cancel out over the oscillation period with the result that the phase difference between the oscillators will be the same at the end of the cycle as it was at the beginning of it. In other words, linear coupling allows no net transfer of energy from one oscillator to another over one cycle. Synchronization is impossible.

Synchronization requires the possibility that energy may be transferred asymmetrically from one oscillator to another due to nonlinearity. For example, if the oscillators have slightly different natural frequencies, the fast oscillator will have to slow down and the slow oscillator will accelerate in order for both to synchronize. Nonlinearity gives asymmetric pushes and pulls which allow a finite amount of energy to be transferred from the fast to the slow oscillator over one cycle. After a number of cycles the pair becomes synchronized, the phase difference becomes independent of time, energy transfer tends to zero and dissipation is at a minimum. Simply put, the Arnold tongue concept is that the greater the strength of (nonlinear) interaction, the greater the difference in natural frequencies the system is able to synchronize.

In terms of synchronizing the heart-lung system, the superiority in performance of pacing with a non-linear oscillator may be in terms of maintaining a bias to resynchronise, during instantaneous changes in respiration rates/patterns over which synchronisation can be obtained or in relation to other parameters.

The principles of nonlinear science implemented by a neuronal oscillator to synchronize itself to respiration and provide stable RSA pacing in the presence of noise, fluctuations in respiration period and variations in the environment, are described below with reference to FIGS. 3 to 6.

Nonlinearity in the implementation of the synchronization module may be used to synchronize respiration and heart rhythm and minimize energy expenditure. This approach is in contrast to traditional electronics in which practitioners instinctively seek to linearize electrical characteristics about "operating points" and avoid nonlinear effects at all costs. Indeed, such effects are typically seen as a nuisance.

Figure 3:
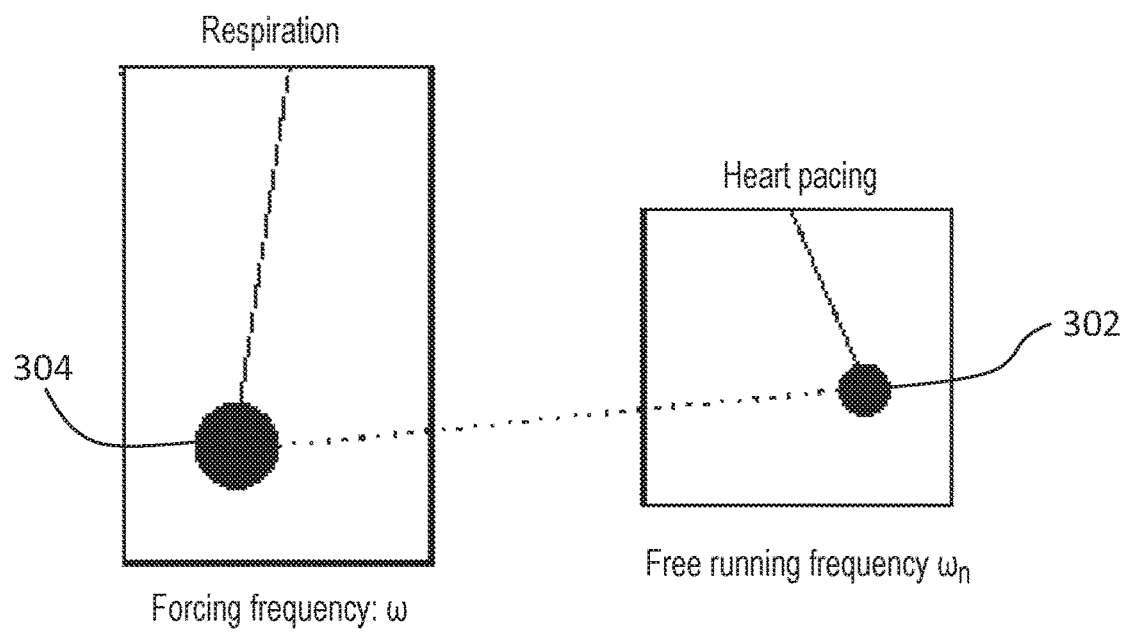
FIG. 3 illustrates a model of synchronization which describes respiration and heart rhythms as two oscillators interacting via a nonlinear spring.

An expanded explanation below, FIG. 3 is a schematic description of the respiratory and cardiac rhythms that interact with one another via the sympathetic nervous system and brainstem neurons (dotted lines). Brain stem biocircuits, neurons, synapses have intrinsic thresholds and nonlinearities (e.g. frequency—current stimulation response). These nonlinearities and heart pacing pendulum oscillator of FIG. 3 form the two main ingredients of the neuronal oscillator. The provision of a neuronal oscillator comprising a single neuron oscillator provides a computationally efficient system for generating pacing timing information.

A neuronal oscillator is only an example of a non-linear oscillator. Any nonlinear oscillator would synchronize to biological rhythms. The neuronal oscillator is a model of the oscillator living systems use. A neuronal oscillator generates "spiky" pulses whose width and period may be tuned independently to meet the specifications of pulse width (typically 1 ms for stimulating the sino-atrial node) and heart pacing frequency. Spike-based neuromorphic models communicate using the same type of communication as biological systems.

A digitally equivalent pacing device may digitally generate the neuronal membrane voltage by solving the Hodgkin Huxley equations (or the mathematical model of the hardware which predicts nearly identical membrane voltage oscillations) to replicate the nonlinear properties to achieve synchronization. This model is given by the following equations:

$$\begin{cases} C\dfrac{dV}{dt} g_{Na}m^3h(E_{Na}-V) + g_Kn^4(E_K-V) + g_L(E_L-V) + I_{inj} & (1) \\ \dfrac{dm}{dt} = \dfrac{m_\infty(V)-m}{t_{0,m}+\epsilon_m\left[1-\tanh^2\dfrac{V-V_{tm}}{\delta V_{\tau m}}\right]}, m_\infty(V) = 0.5\left[1+\tanh\dfrac{V-V_{tm}}{\delta V_m}\right] \\ \dfrac{dh}{dt} = \dfrac{h_\infty(V)-h}{t_{0,h}+\epsilon_h\left[1-\tanh^2\dfrac{V-V_{th}}{\delta V_{\tau h}}\right]}, h_\infty(V) = 0.5\left[1+\tanh\dfrac{V-V_{th}}{\delta V_h}\right] \\ \dfrac{dn}{dt} = \dfrac{n_\infty(V)-n}{t_{0,n}+\epsilon_n\left[1-\tanh^2\dfrac{V-V_{tn}}{\delta V_{\tau n}}\right]}, n_\infty(V) = 0.5\left[1+\tanh\dfrac{V-V_{tn}}{\delta V_n}\right] \end{cases}$$

The state variables of this model are (V, m, h, n) respectively the membrane voltage, Na activation gate variable, Na inactivation gate variable, K activation variable. $I_{inj}$ is the injected current produced by the circuit 108.

An exemplar set of parameters for this model is as follows:

| Ion channel | Parameter ID | Value |
|---|---|---|
| | C (µF · cm$^{-2}$) | 1 |
| | ISA(cm$^2$) | 2.9 × 10$^{-4}$ |
| Fast and transient | $g_{Na}$ (mS · cm$^{-2}$) | 69 |
| Sodium current | $E_{Na}$ (mV) | 41 |
| (NaT) | $V_{tm}$ (mV) | −39.92 |

-continued

| Ion channel | Parameter ID | Value |
|---|---|---|
| | $\delta V_m$ (mV$^{-1}$) | 10 |
| | $t_{0m}$ (mS) | 0.143 |
| | $\epsilon_m$ (mS) | 1.099 |
| | $\delta V_{\tau m}$ (mV$^{-1}$) | 23.39 |
| | $V_{th}$ (mV) | −65.37 |
| | $\delta V_h$ (mV$^{-1}$) | −17.65 |
| | $t_{0h}$ (mS) | 0.701 |
| | $\epsilon_h$ (mS) | 12.9 |
| | $\delta V_{\tau h}$ (mV$^{-1}$) | 27.22 |
| Transient | $g_K$ (mS · cm$^{-2}$) | 6.9 |
| depolarisation | $E_K$ (mV) | −100 |
| activated current | $V_{tn}$ (mV) | −34.58 |
| (K) | $\delta V_{\tau n}$ (mV$^{-1}$) | 23.39 |
| | $\delta V_n$ (mV$^{-1}$) | 22.17 |
| | $t_{0n}$ (mS) | 1.291 |
| | $\epsilon_n$ (mS) | 4.314 |
| Leak current (L) | $g_L$ (mS · cm$^{-2}$) | 0.465 |
| | $E_L$ (mV) | −65 |

The above differential system can be integrated using a microprocessor in a variety of ways but preferably using the adaptive step size odeint( ) routine available in Python or which can be programmed in (see Numerical Recipes in C: The Art of Scientific Computing, Press, Teukolsky, Vetterling, Flannery, CUP, ISBN 0-521-43108-5, Chapter 16).

Some advantages might arise from a digital solution rather than an analogue solution. For example, temperature dependence of operation may be eliminated.

FIG. 3 illustrates the simplest model of synchronization which describes respiration and heart rhythms as two oscillators interacting via a nonlinear spring (dotted lines) The system has a free running oscillator (heart pacing) 302 with natural frequency $\omega_0$ and a forcing oscillator (respiratory) 304 with forcing frequency $\omega$. Modulation of heart pacing by respiration is repeated from one breathing cycle to the next hence needs to be synchronized to the breathing rate otherwise modulation will fluctuate from one period to the next.

When no RSA is imposed (RSA=0), the oscillators 302, 304 are decoupled and the heart pacing oscillator is free running at angular frequency $\omega_0$(I). Coupling is switched on when RSA becomes finite, that is, when different pacing frequencies are applied in the inspiratory and the expiratory phases $f_{insp} \neq f_{exp}$. In this case the free running oscillator will phase lock to the forcing oscillator over synchronization windows of finite width $\Delta\omega$ which enables stable RSA in noisy and variable conditions of respiratory rate.

A neuronal oscillator is an example of a nonlinear oscillator which provides an output frequency in accordance with an injection current (I). The neuronal oscillator has two properties which may assist in providing synchronization:
 (i) Threshold: The neuron is silent up to a threshold current injection ($I_{th}$). Above the threshold $I_{th}$, the neuron oscillates at a frequency that increases nonlinearly with the injection current I so that $\omega_0 = \omega_0(I)$ (See FIG. 7, discussed below). The non-linearity of the $\omega_0(I)$ response is essential as it effectively introduces a decision mechanism for latching the forcing oscillator to the free running oscillator. An oscillator with a perfectly linear $\omega_0(I)$ response would not synchronize.
 (ii) Phase response curve: Synchronization means the adjustment of the rhythm of the free running oscillator to that of the forcing oscillator so that the phase difference between the two oscillators is constant over time. However, there would be little point if synchronization would occur when $\omega = \omega_0$. The instantaneous bias/force towards synchronization is different at different points of the cycle and this dependence is the phase response curve. This property of the neuron enables phase locking to occur over a wider frequency range $\Delta\omega$ centred on $\omega_0$ is the phase response curve.

A nonlinear oscillator such as the neuron is not a harmonic oscillator but oscillates as prescribed by the 4 differential equations of the Hodgkin-Huxley model, Eq. 1. The dynamics resulting from these 4 equations tends to pull the phase of the free running oscillator towards the phase of the forcing oscillator when their frequencies are close to one another. This enables synchronization to occur over a range of frequency $\Delta\omega$ centred on $\omega_0$.

Figure 4A:
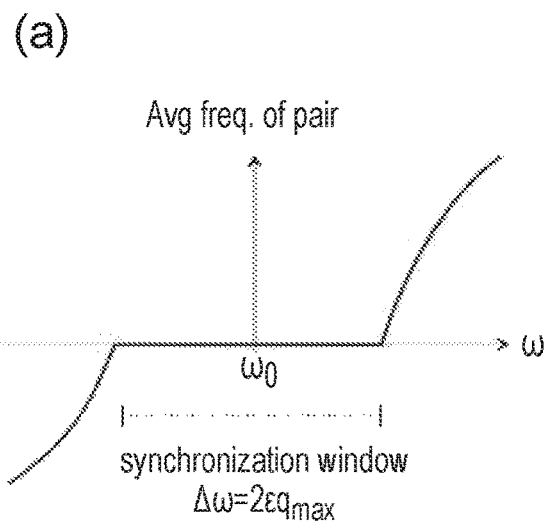
FIG. 4a illustrates an average resultant frequency of the forcing oscillator and free running oscillator as a function of the free running frequency for a particular forcing frequency.

FIG. 4a illustrates the average resultant frequency of the forcing oscillator and free running oscillator as a function of the free running frequency for a particular forcing frequency. The forcing oscillator (respiration) synchronizes with the pacing oscillator (neuron) over a finite frequency window $\Delta\omega$ centred on the free running frequency of the pacing oscillator.

Mathematically, the phase pull due to anharmonicity is described by a phase dependent function known as the phase response curve of the neuron and noted $q(\Delta\phi)$ where $\Delta\phi$ is the phase difference between the forcing and free running oscillators. The evolution of the phase difference between the two oscillators is:

$$\frac{d\Delta\phi}{dt} = (\omega_0 - \omega) + \varepsilon q(\Delta\phi) \quad (2)$$

Figure 4B:
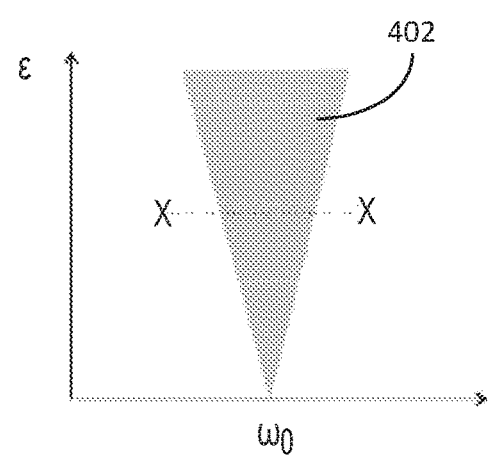
FIG. 4b illustrates an 'Arnold tongue', a widening of the synchronization window as the coupling strength between the two oscillators increases.

FIG. 4b illustrates the 'Arnold tongue' 402, a widening of the synchronization window as the coupling strength ($\varepsilon$) between the two oscillators increases. The "pull" of the dephasing by phase response curve means that the neuron will remain synchronized to the respiration over a finite range of forcing frequency namely, $|\omega_0-\omega|<\varepsilon q_{max}$.

Synchronization can minimize energy dissipation in the coupled oscillator system. If the heart-lung system dissipates less energy through RSA synchronization, the energy saving can be used elsewhere and may be directed to increase cardiac output.

Nonlinear coupling induces synchronization by allowing asymmetric pushes and pulls of one oscillator on the other. As a result, oscillator phases lock after a number of cycles. The "pushes and pulls" at each point of the cycle are determined by the phase response curve (Eq. 2). In energy terms, nonlinearity allows a finite amount of energy to be transferred from the fast oscillator to the slow oscillator over one cycle. After a number of cycles, energy transfer stops when the oscillators oscillate in phase (same frequency).

The mechanism of respiratory sinus arrhythmia modulates heart rate over the respiratory cycle. In addition to the respiratory frequency w and the base heart rate frequency $\omega_{exp}$ (or $\omega_0$ of FIG. 3), one introduces the heart rate frequency during the inspiratory part of the duty cycle, $\omega_{insp}$ ($\omega_{insp}>\omega_{exp}$). Then RSA is defined as:

$$RSA = \frac{\omega_{insp} - \omega_{exp}}{\omega_{exp}} \quad (3)$$

Figure 5:
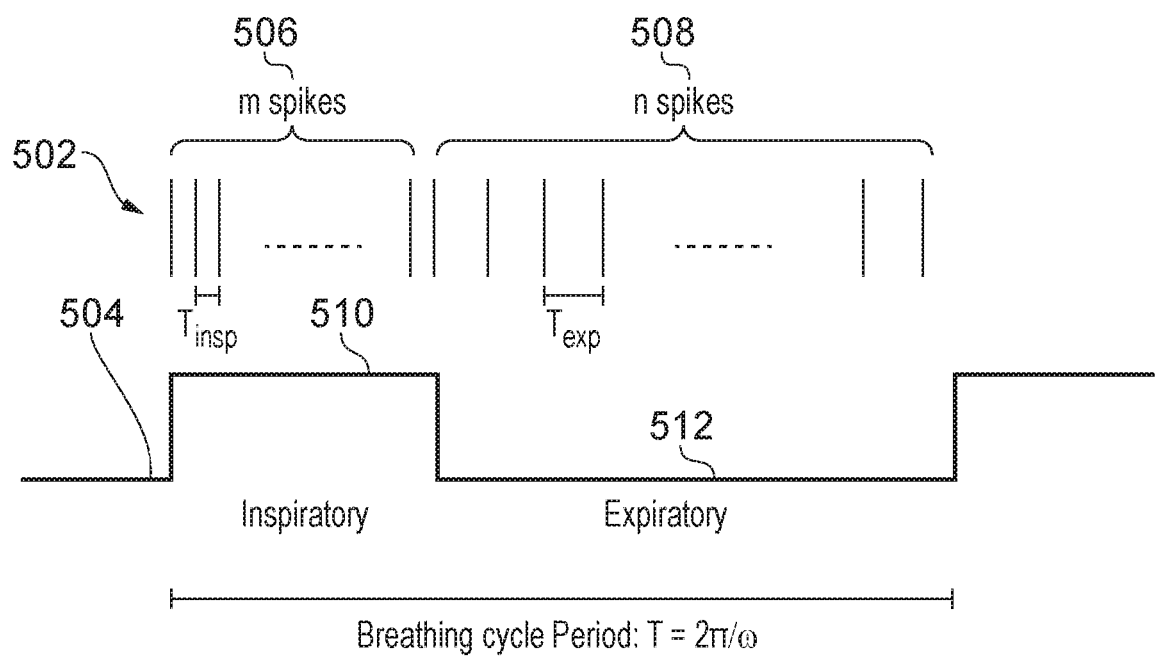
FIG. 5 illustrates a sequence of electrical stimuli for the heart as a function of time together with a corresponding respiration duty cycle.

This modulation of cardiac frequency over the respiratory cycle is shown in FIG. 5.

FIG. 5 illustrates a sequence of electrical stimuli 502 for the heart as a function of time together with a corresponding respiration duty cycle 504. When dealing with RSA there is more than a single combination of inspiratory and expiratory frequencies that give a sequence of interspike intervals fitting in the respiration period (FIG. 5). The respiration duty cycle 504 has an inspiratory phase 510 and an expiratory phase 512. Each electrical stimulus of the stimuli 502 is associated with an electrical stimulus period.

There are m electrical stimulus periods $T_{insp}$ 506 during inspiratory phase 510 and n electrical stimulus periods $T_{exp}$ 508 during expiratory phase 512, which fit within a single breathing period:

$$T=mT_{insp}+nT_{exp} \quad (4)$$

Making the substitution: $T_{exp}=2\pi/\omega_{exp}$, $T_{insp}=2\pi/[\omega_{exp}(1+RSA)]$, where $RSA=(\omega_{insp}-\omega_{exp})/\omega_{exp}$, gives the following manifold of synchronization frequencies (m, n=1,2,3, . . . ):

$$\omega = \frac{\omega_{exp}}{\left(n + \frac{m}{1+RSA}\right)} \quad (5)$$

Under a set RSA amplitude and heart pacing frequency, the respiration rate enabling: $f_{exp}$=90 bpm ($T_{exp}$=0.666 s) and $f_{insp}$=110 bpm ($T_{insp}$=0.545 s) gives the following discrete frequencies of synchronization, for example.

| No. Pacing pulses per respiration period | No. Pacing pulses in Expiratory phase n | No. Pacing pulses in inspiratory phase m | Breathing period, T $[nT_{exp} + mT_{insp}]$ (seconds) | Breathing rate, $\omega$, for sync to occur (bpm) |
|---|---|---|---|---|
| 2 | 1 | 1 | 1.213 | 49.5 |
| 3 | 1 | 2 | 1.756 | 34.2 |
| 3 | 2 | 1 | 1.877 | 32.0 |
| 4 | 1 | 3 | 2.301 | 26.0 |
| 4 | 2 | 2 | 2.426 | 24.7 |
| 4 | 3 | 1 | 2.543 | 23.6 |
| 5 | 1 | 4 | 2.846 | 21.1 |
| 5 | 2 | 3 | 2.967 | 20.2 |
| 5 | 3 | 2 | 3.088 | 19.5 |
| 5 | 4 | 1 | 3.209 | 18.7 |

Figure 6:
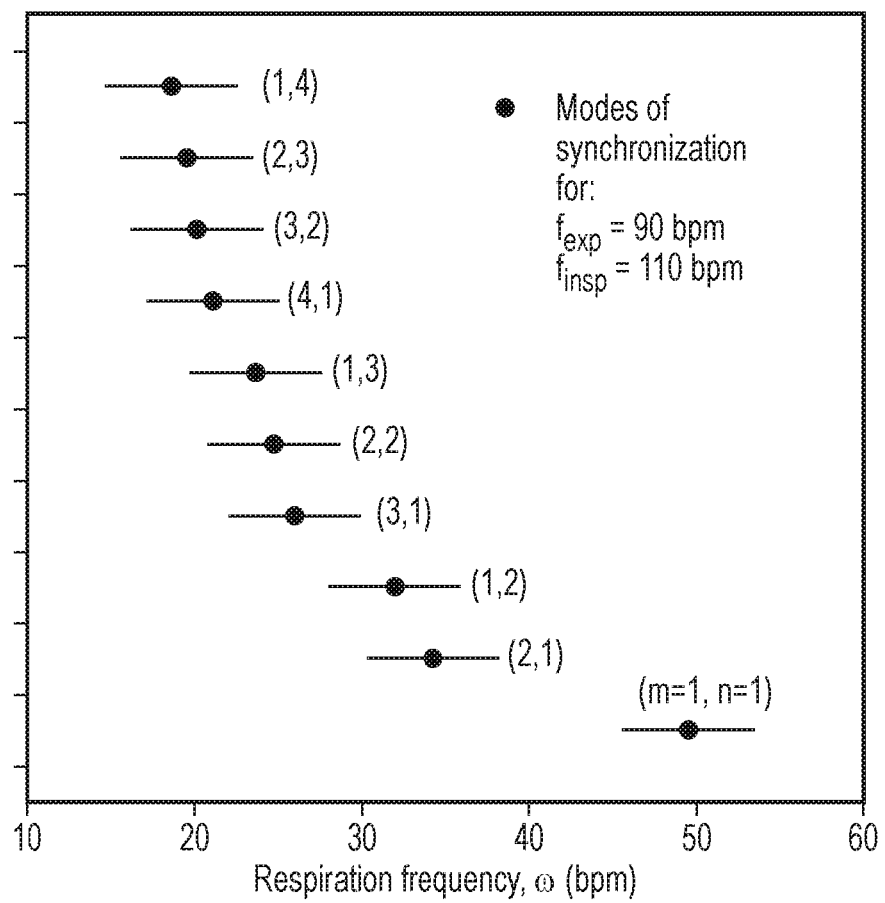
FIG. 6 shows discrete synchronization frequencies separated by frequency gaps during which heart rate modulation may fluctuate randomly.

FIG. 6 shows discrete synchronization frequencies (at points) separated by frequency gaps during which heart rate modulation may fluctuate randomly. The horizontal bars in FIG. 6 show the widths of the Arnold tongues for the specific RSA parameters. The finite intervals of phase locking enable stable RSA.

Figure 7:
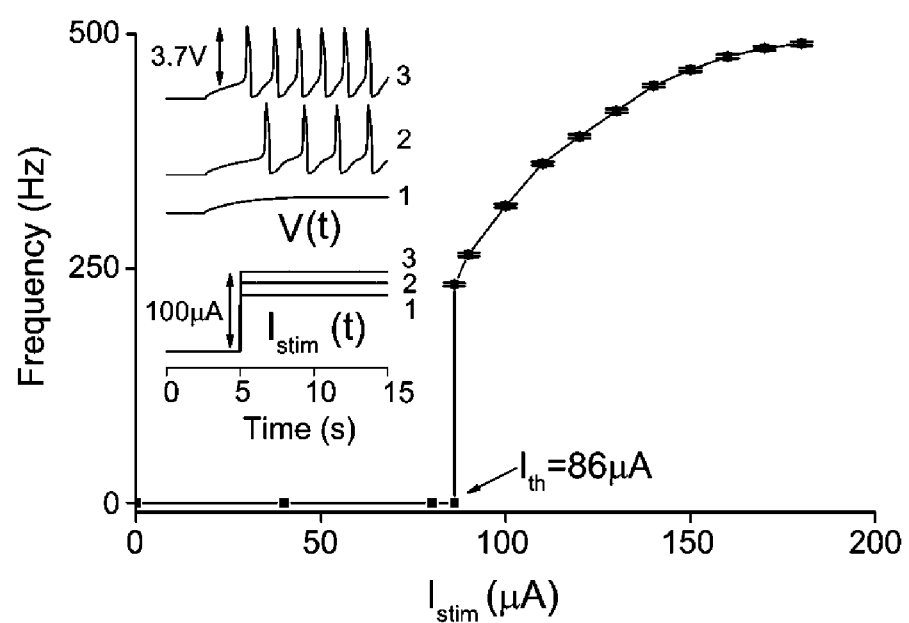
FIG. 7 shows the dependence of frequency of oscillation of the neuron membrane voltage as a function of injected current.

A neuronal oscillator has a frequency that increases as a function of current injection as shown in FIG. 7. Therefore, the strength of coupling, or $RSA=(f_{insp}-f_{exp})f_{exp}$, is set by varying the amount of current injected in the neuron during the inspiratory part of the cycle ($I_{insp}$) relative to the current applied in the expiratory part of the cycle ($I_{exp}$). The current difference ($I_{insp}-I_{exp}$) may be set, by a user for example, to control the strength of coupling.

FIG. 7 shows the dependence of frequency of oscillation of the neuron membrane voltage as a function of injected current: $f(I_{inj})$ from a numerical simulation of pacemaker oscillations. RSA is generated by injecting in the neuron a rectangular current signal with two levels $I_{insp}$ and $I_{exp}$ which set frequencies $f_{insp}$ and $f_{exp}$. Both $I_{insp}$ and $I_{exp}$ are greater than the threshold $I_{th}$. Because the neuron oscillation frequency increases with current injection, the strength of $RSA=(f_{insp}-f_{exp})/f_{exp}$ is increased or decreased by increasing $I_{insp}$ relative to $I_{exp}$.

The main source of nonlinearity in the neuron response is the frequency-current dependence illustrated in FIG. 7. In biological implementations, this nonlinear dependence is underpinned by the sigmoidal activation and inactivation curves of sodium and potassium ion channels in the neuron membrane, each of which has an activation threshold. The dynamics of sodium and potassium ionic currents may be modelled by the neuron electronics.

Figure 15:
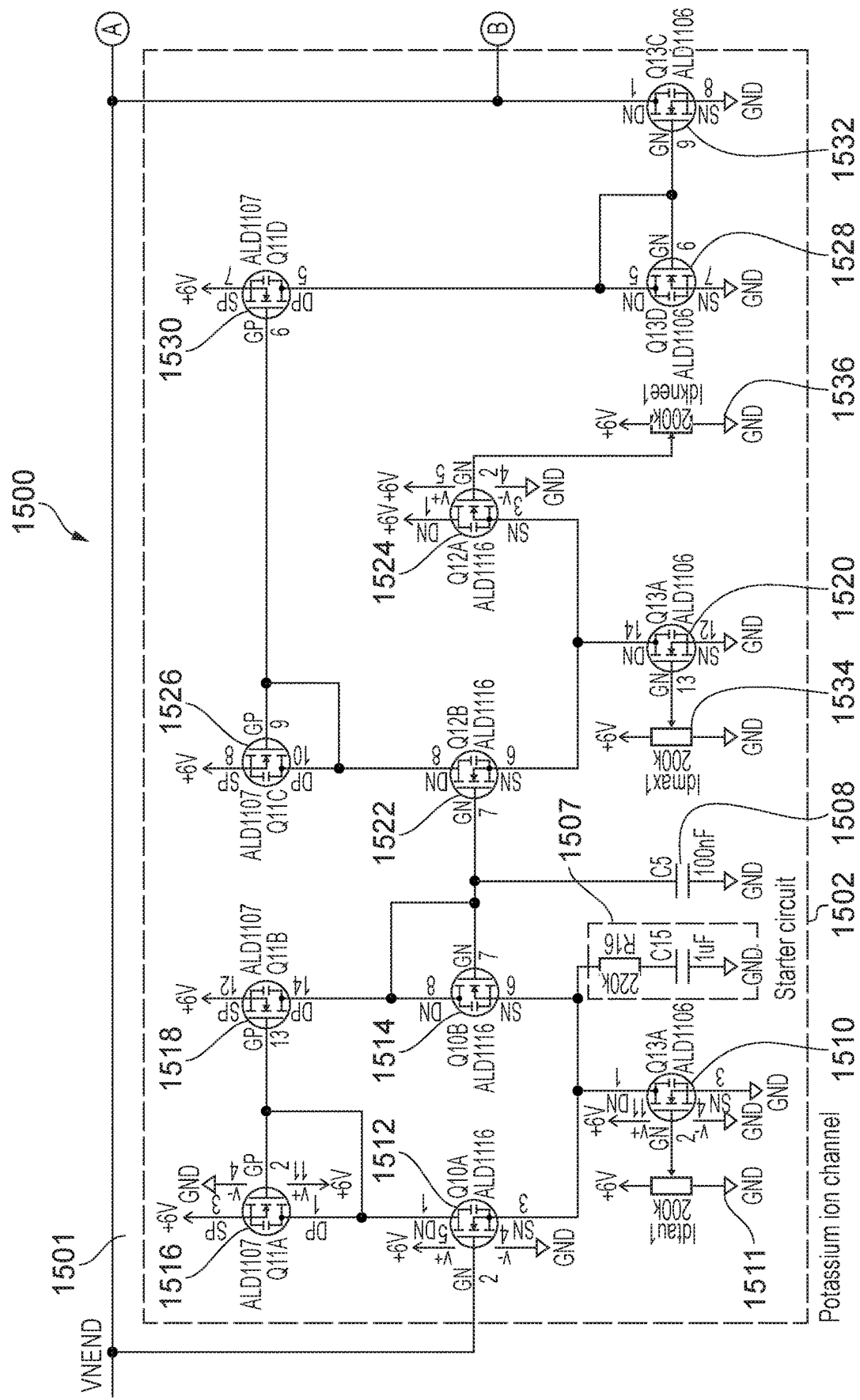
FIG. 15 illustrates an example implementation of a neuronal oscillator.
Figure 15:
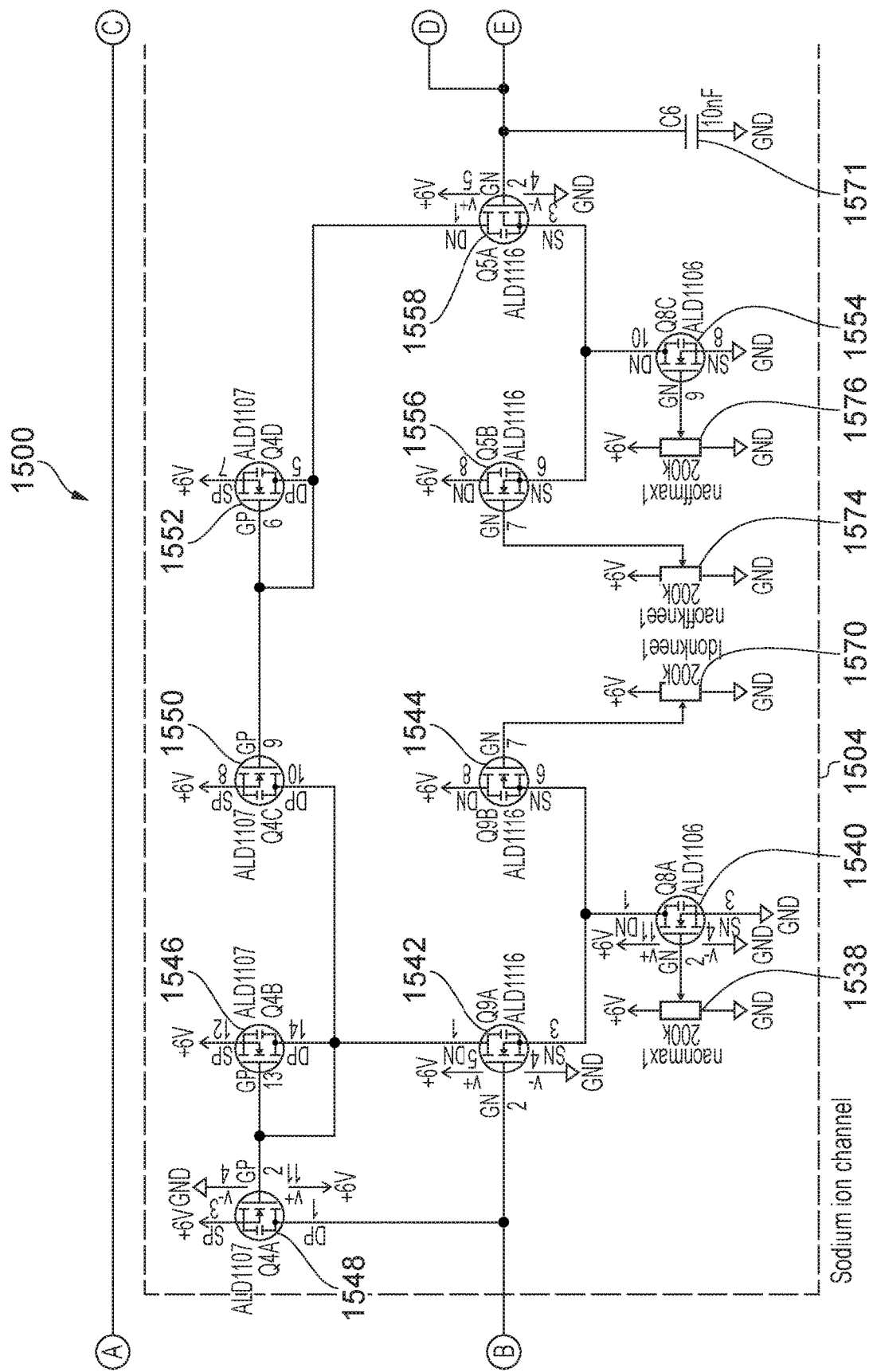
Figure 15:
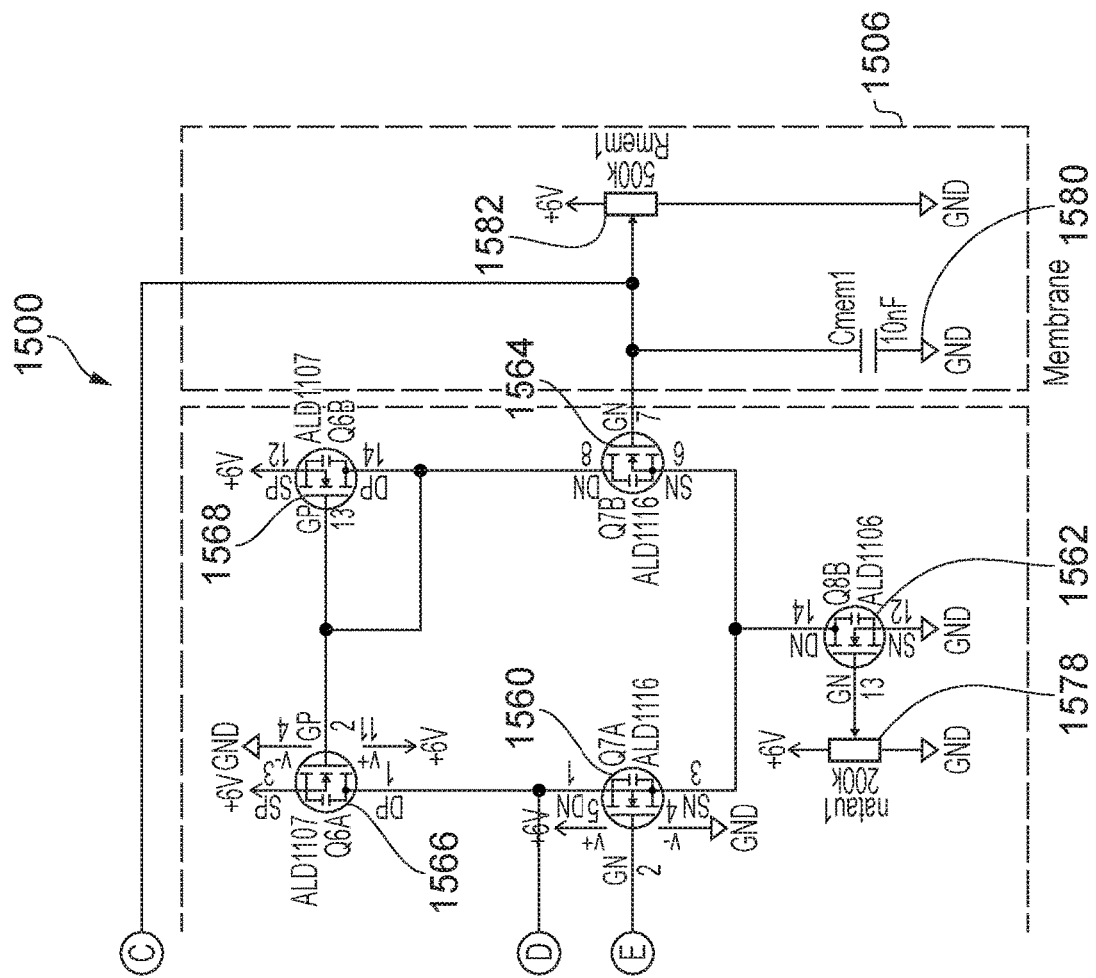

FIG. 15 illustrates an example implementation of a neuronal oscillator 1500. The neuronal oscillator 1500 is provided by analogue electronics configured to mimic the behaviour of a neuron. The neuronal oscillator 1500 has a potassium ion channel section 1502, a sodium ion channel section 1504 and a membrane section 1506 to model the corresponding ion channels of a neuron cell. The neuronal oscillator 1500 provides a membrane voltage as an output on an output rail 1501

The potassium ion channel section 1502 comprises a plurality of field effect transistors (FETs), a plurality of variable voltage sources, a starter circuit 1507 and a timing capacitor 1508 determining the recovery rate of the potassium activation gate. The plurality of FETs comprises first, second, third, fourth, fifth, sixth, seventh, eighth, ninth, tenth, and eleventh and twelfth FETs 1510-1532. Each FET 1510-1532 has a gate, a source and a drain.

The variable voltage sources, which may be used to set the conditions of the neuron, may be provided by a potential divider formed by a potentiometer. These voltage sources are used to set the voltage thresholds $V_{tm}$, $V_{th}$, $V_{tn}$ and conductances $g_{Na}$ and $g_k$ mentioned in the Table above.

The gate of the first FET 1510 is coupled to a voltage source 1511. The source of the first (n-type) FET 1510 is coupled to ground, the drain of the first FET 1510 is coupled to the source of the second (n-type) FET 1512, to the source of the third (n-type) FET 1514 and the starter circuit 1507.

The starter circuit 1507 comprises an RC timing circuit provided by a resistor and a capacitor in series between the drain of the first FET 1510 and ground.

The gate of the second FET 1512 is coupled to the rail 1501 (the membrane voltage $V_{mem}$)

The source of the fourth (p-type) FET 1516 and the source of the fifth (p-type) FET 1518 are coupled to the positive voltage source. The gate of the fourth FET 1516 is coupled to the gate of the fifth FET 1518. The drain of the fourth FET 1516 is coupled to the gate of the fourth FET 1516 and the drain of the second FET 1512. The drain of the fifth FET 1518 is coupled to the drain of the third FET 1514. The gate of the third FET 1514 is coupled to the drain of the third FET 1514 and the gate of the sixth (n-type) FET 1522. The timing capacitor 1508 is coupled between the gate of the third FET 1514 and ground.

The source of the twelfth (n-type) FET 1520 is coupled to ground. The gate of the twelfth FET 1520 is coupled to second voltage source 1534. The drain of the twelfth FET 1520 is coupled to the source of the sixth (n-type) FET 1522 and the source of the seventh (n-type) FET 1524. The gate of the seventh FET 1524 is coupled to a third voltage source 1536 which sets the Potassium activation threshold. The drain of the seventh FET 1524 is coupled to the positive voltage source. The source of the eighth (p-type) FET 1526 is coupled to the positive voltage source. The gate of the eighth FET 1526 is coupled to the drain of the eighth FET 1526, the drain of the sixth FET 1522 and the gate of the ninth (p-type) FET 1530. The source of the ninth FET 1530 is coupled to the positive voltage source.

The source of the tenth (n-type) FET 1528 is coupled to ground. The gate of the tenth FET 1528 is coupled to the drain of the drain tenth FET 1528, the drain of the ninth FET 1530 and the gate of eleventh (n-type) FET 1532. The source of the eleventh FET 1532 is coupled to ground. The drain of the eleventh FET 1532 is coupled to the rail 1501 and the sodium ion channel section 1504.

The sodium ion channel section 1504 also comprises a plurality of field effect transistors (FETs) 1540-1568, a plurality of variable voltage sources and a timing capacitor 1571. The plurality of FETs comprises first, second, third, fourth, fifth, sixth, seventh, eighth, ninth, tenth, eleventh, twelfth, thirteenth, fourteenth and fifteenth FETs 1540-1568. Each FET 1540-1568 has a gate, a source and a drain.

The first (n-type) FET 1540 has a source coupled to ground. The first FET 1540 has a gate coupled to the first variable voltage source 1538. The first FET 1540 has a drain coupled to the source of the second (n-type) FET 1542 and the source of the fifteenth (n-type) FET 1544. The gate of the second FET 1542 is coupled to the rail 1501 and the potassium ion channel section 1502. The gate of the second FET 1542 is also coupled to the drain of the fourth (p-type) FET 1548. The source of the fourth FET 1548 is coupled to the positive voltage source. The gate of the fourth FET 1548 is coupled to the gate of the third (p-type) FET 1546, the drain of the third FET 1546 and the drain of the fifth (p-type) FET 1550. The source of the third FET 1546 is coupled to the positive voltage source. The source of the fifth FET 1550 is coupled to the positive voltage source.

The drain of the fifteenth (n-type) FET 1544 is coupled to the rail 1501. The gate of the fifteenth FET 1544 is coupled to the second variable voltage source 1570 that sets the activation threshold of the sodium channel The gate of the sixth (p-type) FET 1552 is coupled to the drain of the sixth FET 1552 and the gate of the fifth FET 1550. The source of the sixth FET 1552 is coupled to the positive voltage source.

The source of the seventh FET is coupled to ground. The gate of the seventh (n-type) FET 1554 is coupled to the third variable voltage source 1576. The drain of the seventh FET 1554 is coupled to the source of the eighth (n-type) FET 1556 and the source of the ninth (n-type) FET 1558. The drain of the ninth FET 1558 is coupled to the drain and gate of the sixth FET 1552.

The gate of the eighth FET 1556 is coupled to the fourth variable voltage source 1574, which sets the sodium inactivation threshold. The source of the eighth FET 1556 is coupled to the positive voltage source.

The timing capacitor 1571 is coupled between the gate of the ninth FET 1558 and ground. The gate of the ninth (n-type) FET 1558 is also connected to the gate of the tenth (n-type) FET 1560, the drain of the tenth FET 1560 and the drain of the thirteenth (p-type) FET 1566. The source of the thirteenth FET 1566 is coupled to the positive voltage source.

The source of the eleventh (n-type) FET 1562 is coupled to ground. The gate of the eleventh FET 1562 is coupled to the fifth variable voltage source 1578. The drain of the eleventh FET 1562 is coupled to the source of the tenth (n-type) FET 1562 and the source of the twelfth (n-type) FET 1564. The drain of the twelfth FET 1564 is coupled to the drain of the fourteenth (p-type) FET 1568, the gate of the fourteen FET 1568 and the gate of the thirteenth FET 1566.

The gate of the twelfth FET 1564 is connected to the membrane section 1506. The membrane section 1506 comprises a membrane capacitor 1580 and a leakage resistance 1582 of the neuron membrane. The membrane capacitor 1580 is coupled between the gate of the twelfth FET 1564 of the sodium ion channel section 1504 and ground. The gate of the twelfth FET 1564 is also coupled to the rail 1501 and the leakage resistance of the neuron membrane 1582 within the membrane section 1506.

Considerations in setting, in a neuronal oscillator, a parameter (RSA=$(f_{insp}-f_{exp})/f_{exp}$) determining a differential stimulus signal rate between the inspiration and expiration phases, and setting a strength of coupling factor to determine (i) a speed of synchronization between the nonlinear oscillator and the respiration duty cycle signal and/or (ii) a tolerance to frequency mismatch between the respiration period and one or more target heart beat intervals are discussed below with reference to FIGS. 8 to 10.

Figure 8A:
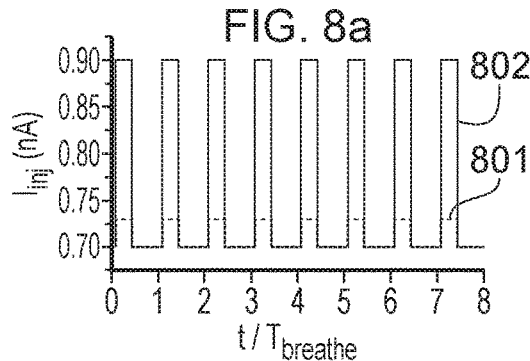
FIG. 8a illustrates rectangular modulation of input current applied at the input to the neuronal oscillator against time divided by the breath period.
Figure 8C:
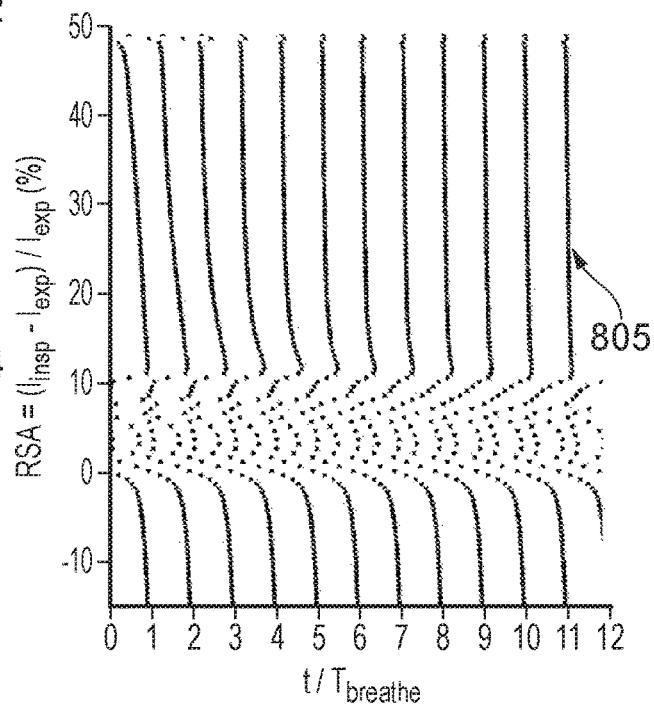
FIG. 8c illustrates timings of heart stimulations plotted as an amplitude of RSA against time divided by the breath period.
Figure 8B:
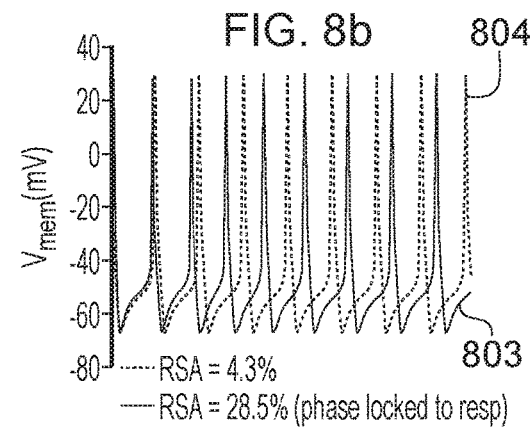
FIG. 8b illustrates pacing pulse profiles against time divided by the breath period corresponding to the rectangular modulation of input current.

FIGS. 8a to 8c relate to an example in which the breathing frequency (RR) is identical to the base heart rate (HR) giving HR/RR=1.

FIG. 8a illustrates rectangular modulation of input current 801, 802 applied at the input to the neuronal oscillator against time divided by the breath period. Oscillations of the pacemaker neuron and the corresponding rectangular waveform are plotted for two RSA levels of 4.3% (801) and 28.5% (802).

FIG. 8b illustrates corresponding pacing pulse profiles for the two RSA levels of 4.3% (803) and 28.5% (804) against time divided by the breath period. Heart beats synchronize to respiration within a couple of heart beats. This bias to synchronization is stronger as RSA increases. In particular, where the RSA=28.5% the trace 804 is almost fully synchronized from t=0 unlike the RSA=4.3% trace 803.

FIG. 8c illustrates the timings of heart stimulations plotted as an amplitude of RSA against time divided by the breath period. When t<0, the neuron is stimulated with constant current $I_e$=0.5 nA producing oscillations with base period of 25.579965 ms. At t=0, rectangular current modulation is applied.

When RSA<10% the coupling is too weak to force the neuron to fire in phase with respiration (compare profile 803 with 801 and the rapidly shifting phase of oscillations in FIG. 8c). A transient regime is about 3 periods long. In this small RSA regime, the system adapts through rapid shifts in the dephasing of oscillations as a function of RSA (left panel).

When RSA>10%, the phase of oscillations becomes locked to respiration and the frequency of heart rate and respiration are identical (compare profile 802 with 804 and the stable phase of oscillations in FIG. 8b). Despite RSA tending to increase HR, mode locking HR/RR=1 is maintained by the bias to synchronization applied by nonlinearity. This synchronization regime corresponds to the first Arnold tongue. That is, the first of mode locked synchronization plateaux 805 is observed at RSA>10%. Increasing the strength of RSA further from 20% to 50% makes stimuli lock faster to breathing period: the lines are becoming straighter at the left of FIG. 8c as RSA increases.

Figure 9A:
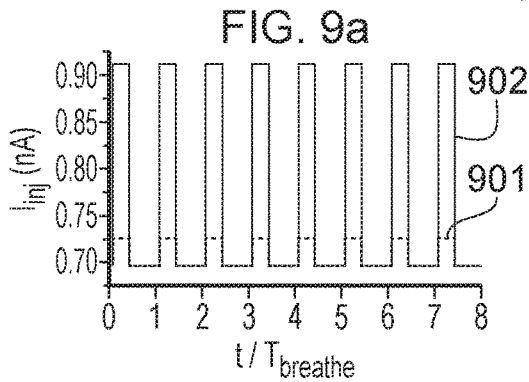
FIGS. 9a to 9c are of the same format as corresponding FIGS. 8a to 8c, and the breathing period is set to twice the base heart period.
Figure 9C:
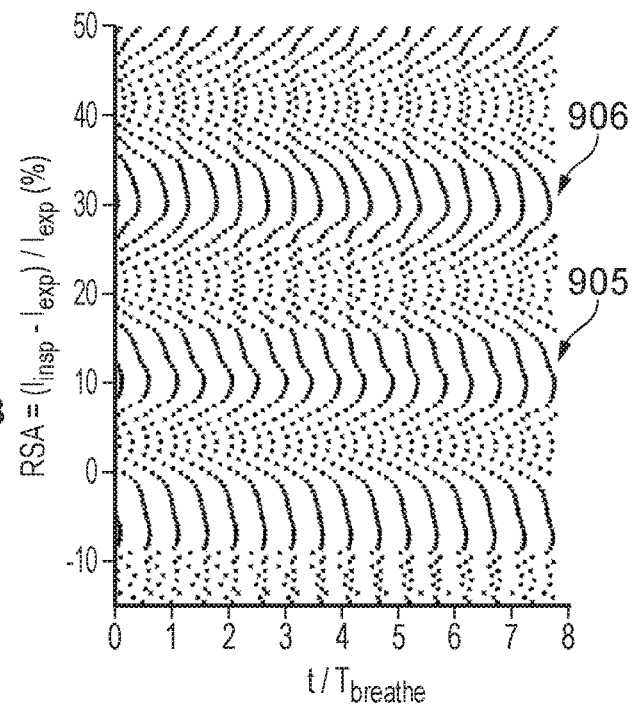
Figure 9B:
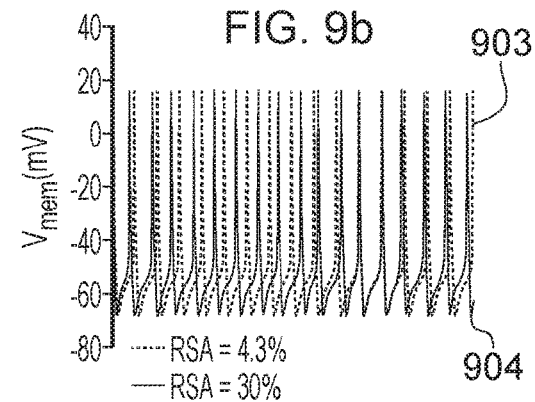

In FIGS. 9a to 9c, the breathing period (RR=51.15993 ms) is set to twice the base heart period (HR=25.579965 ms) giving HR/RR=2. There are two beats per breathing period. FIGS. 9a to 9c are of the same format as corresponding FIGS. 8a to 8c. In FIG. 9b, oscillations of the pacemaker neuron and the corresponding rectangular stimulation waveform (FIG. 9a) are plotted for two RSA levels of 4.3% (901) and 30% (902).

FIG. 9b illustrates corresponding pacing pulse profiles for the two RSA levels of 4.3% (903) and 30% (904). Since square pulse modulation is applied from t=0 in FIG. 9a, the pulse profiles (903, 904) relate to a transient regime evolving towards more stable oscillations after a few breathing cycles. As such, the pulse profiles (903, 904) provide an example of a time period taken to achieve a level of synchronization.

In FIG. 9c, multimodal mode locked synchronization 905, 906 is observed at RSA~10%, 30% separated by regions where beat-to-beat frequency modulation and base heart frequency are maintained across the respiration period but the phase of oscillations is not mode locked to respiration (regions of rapid phase shifts centred on RSA=5%, 22%, 42% . . . ).

Figures 10A, 10B, 10C:
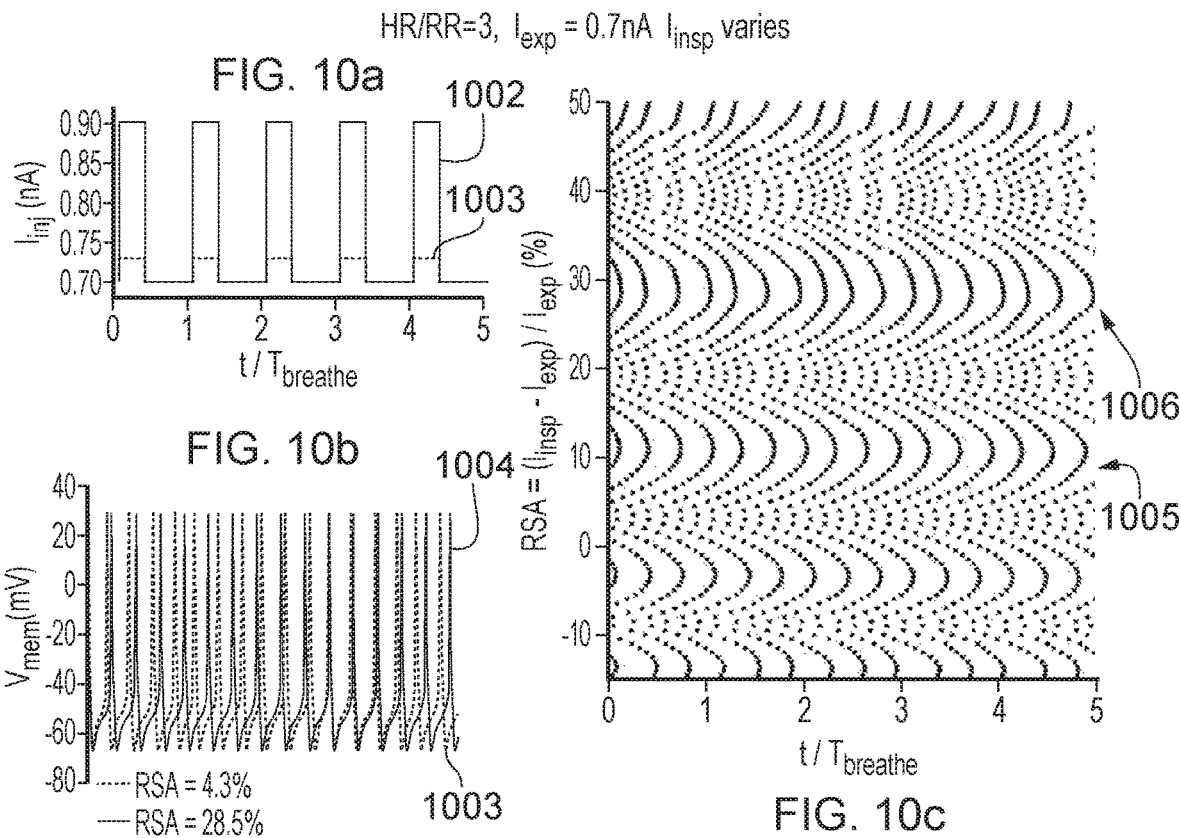
FIGS. 10a to 10c are of the same format as corresponding FIGS. 8a to 8c, and the breathing period is set to thrice the base heart period.

FIGS. 10a to 10c are of the same format as corresponding FIGS. 8a to 8c. There are three beats per breathing period. The breathing period (RR=76.739895 ms) is set to trice the base heart period (HR=25.579965 ms) giving HR/RR=3. In FIG. 10b, oscillations of the pacemaker neuron and the corresponding rectangular stimulation waveform (FIG. 10a) are plotted for two RSA levels of 4.3% (1001) and 28.5% (1002).

FIG. 10b illustrates corresponding pacing pulse profiles for the two RSA levels of 4.3% (1003) and 28.5% (1004).

In FIG. 10c, multimodal mode locked synchronization 1005, 1006 is observed at RSA~10%, 30% separated by regions where beat-to-beat frequency modulation and base heart frequency are maintained across the respiration period but the phase of oscillations is not mode locked to respiration (phase shifts).

Figure 11:
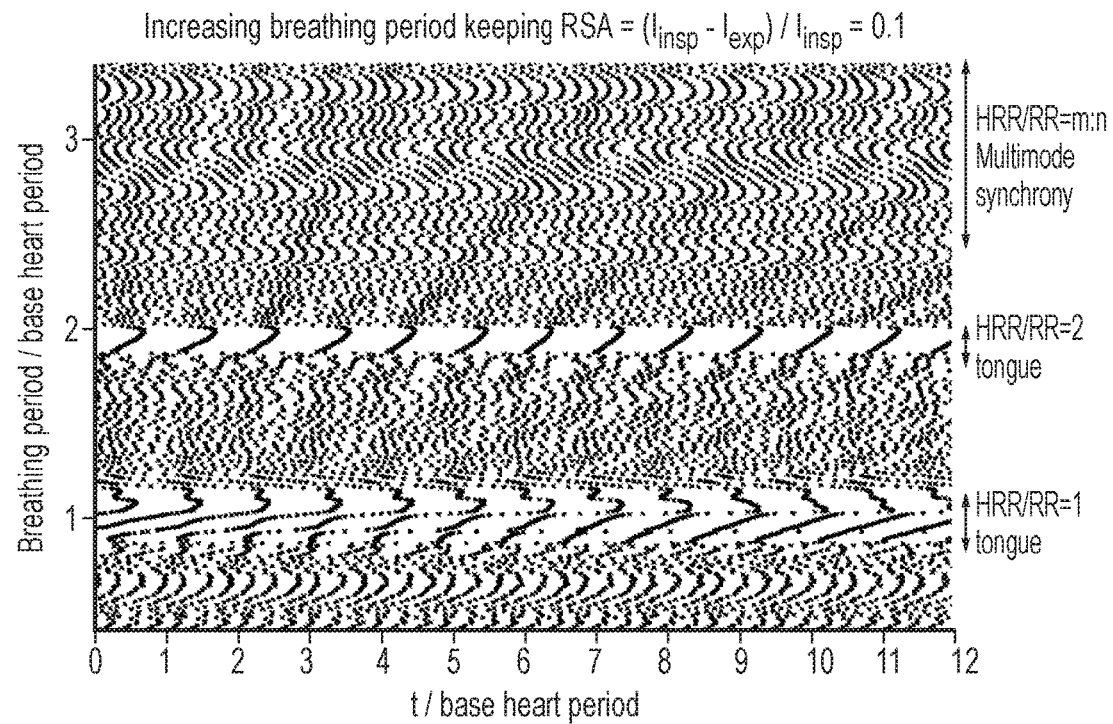
FIG. 11 illustrates a profile of breathing period to base heart period ratio against time divided by the base heart period, in which the RSA value is 0.1.
Figure 12:
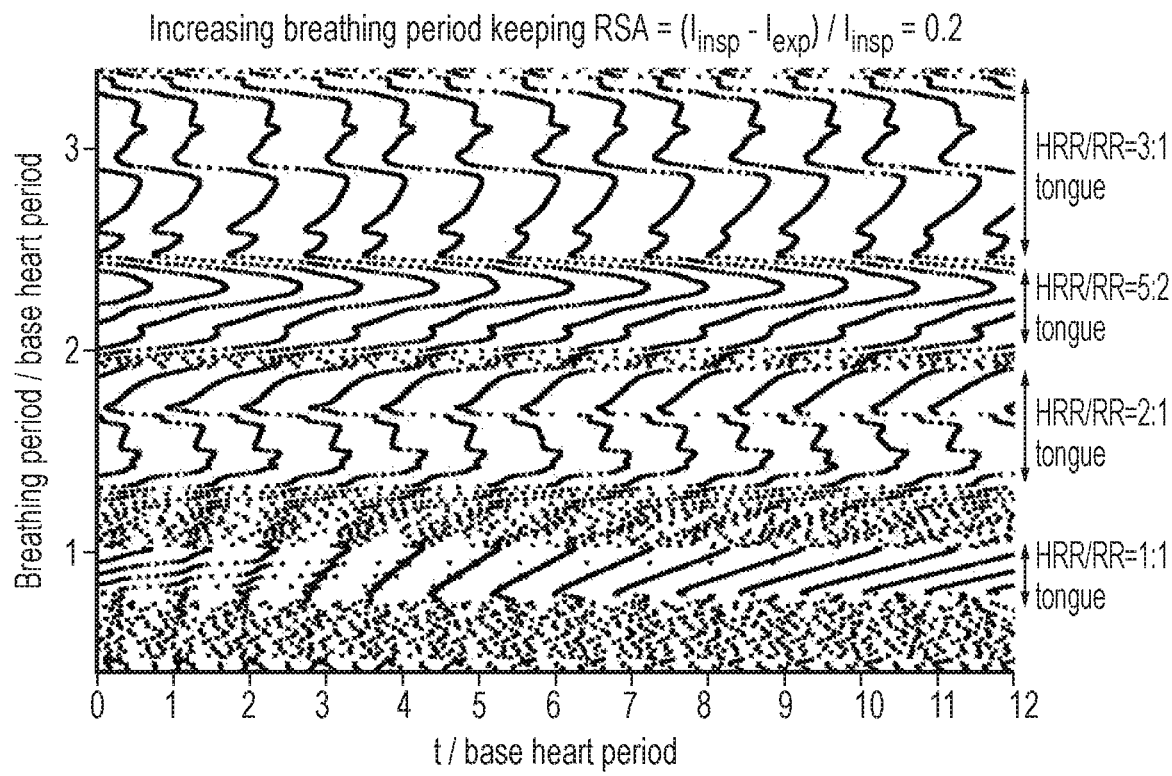
FIG. 12 illustrates a profile of breathing period to base heart period ratio against time divided by the base heart period, in which the RSA value is 0.2.
Figure 13:
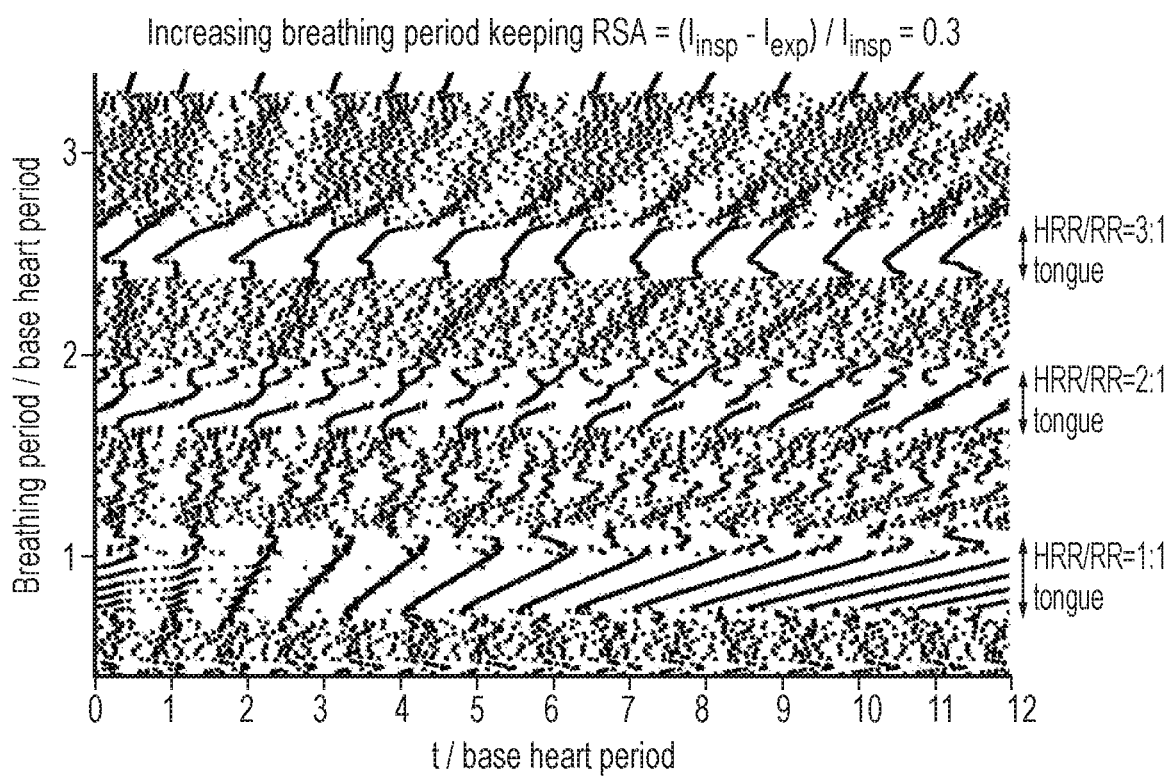
FIG. 13 illustrates a profile of breathing period to base heart period ratio against time divided by the base heart period, in which the RSA value is 0.3.

FIGS. 11 to 13 illustrate profiles of breathing period to base heart period ratio against time divided by the base heart period (25.679965 ms). In FIG. 11, the RSA value is 0.1. In FIG. 12, the RSA value is 0.2. In FIG. 13, the RSA value is 0.3. FIGS. 11 to 13 therefore illustrate stimulation patterns of a system going through different mode-locked oscillations as the ratio of the breathing period relative to the base heart frequency increases.

Regions of multimodal synchrony and HR/RR Arnold tongue values are illustrated on the profiles, demonstrating the ability of the method to adjust under changing respiration period to maintain a bias towards synchronization between the respiration period and an integer multiple of the stimulus signals periods. Increasing RSA from 0.1 to 0.3 increases the width of synchronization plateaux, the first Arnold tongue. Increasing RSA also appears to reduce the occurrence of multimode synchronization. In between regions of synchronization, the phase of heart oscillations change rapidly relative to the respiration rhythm however the modulation of heart rate is maintained.

These results show that plateaux of mode locked synchronization form when HR/RR=1, 2, 3 . . . (integer values). Within these plateaux the pacing frequency is mode locked to the respiration frequency (phase between the two is constant), beat-to-beat heart frequency modulation occurs. In between synchronization plateaux, the phase of heart beats is not mode locked to respiration anymore, showing rapid changes as RSA changes. Respiration still modulates heart rate but the beat pattern changes from one respiration cycle to the next.

The analogue CPG system may improve the number of RSA (increased frequency) paces that can be applied in any given inspiration window including rapid re-acquisition of synchronisation following changes in respiration pattern, which stops and changes as the animal eats, drinks, exercises, rests, coughs and which also naturally exhibits periods of apnoea etc.

There has been shown to be an improvement in cardiac output well-beyond initial expectation in the small set of animals treated with the trial equipment deployed. This cardiac output also exceeded the cardiac output induced by sinusoidal modulation of the timings of heart stimulation (i.e. with heart rate modulation but no heart-breadth synchronization). As discussed, there is a biological 'energy saving' argument why RSA pacing leads to improved cardiac pumping efficiency and that achieving excellent results depends on achieving high levels of RSA within the constraints imposed by a subject's changing respiration and activity patterns.

Figure 14:
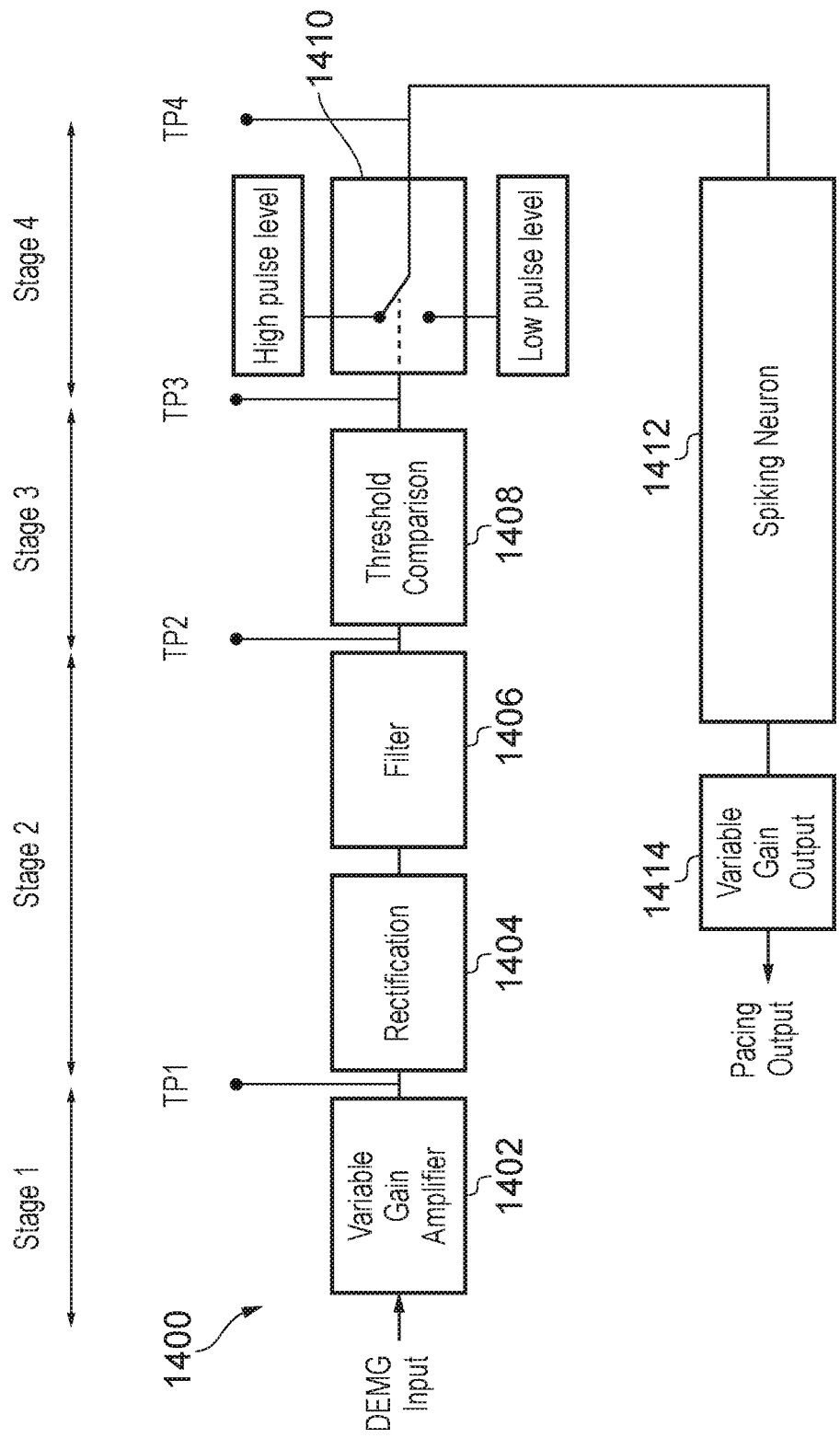
FIG. 14 shows a schematic block diagram of an example cardiac pacing device.

FIG. 14 shows a schematic block diagram of an example cardiac pacing device 1400 such as that described previously with reference to FIG. 1. The cardiac pacing device 1400 comprises a linear chain providing the functionality of the signal processing unit and the electrical stimulus generator described previously. The signal processing unit has 5 stages in this example. An input to the first stage may be provided from a dEMG (diaphragmatic electromyography sensor) input. The dEMG is a standard biomedical technique for the detection of the contraction of muscles. The sensors may be implanted in the muscles involved in diaphragm contraction.

In the first stage, a variable gain amplifier 1402 is used to amplify the relatively low amplitude dEMG input signal to provide an amplified signal to the second stage. The variable gain amplifier 1402 may be provided by a low noise, low power amplifier in a differential input configuration to recover the dEMG signal. dEMG involves detection of microvolt level signals (in the range 10 to 100 microvolts) and amplifying them many hundreds of thousands of times. The body is rich in other sources of electrical disturbance (heart beats (ECG), skeletal muscle contractions and relaxations etc.) In pacing applications, the ECG pulse induced by the pacing signal is of the order of tens of millivolts, around 100 to 1000 times stronger than the dEMG signal to be detected and that arises from the contraction of the diaphragm. The second stage comprises a rectification unit 1404 and a filter 1406. The filter 1406 may be a Sallen-Key filter or Butterworth filter, for example. The rectification unit 1404 is configured to recover, through rectification, a respiration signal from the amplified signal. The filter 1406 is configured to filter the rectified signal to reduce noise. The output of the filter 1406 is provided to a third stage.

In the third stage, a threshold comparator 1408 is provided. The threshold comparator 1408 is configured to determine whether the respiration signal is associated with an inspiration phase or an expiratory phase. The output of the threshold comparator 1408 is used to control a switching device 1410 in the fourth stage. The switching device 1410 may output a rectangular current profile similar to the one shown in FIGS. 8a, 9a and 10a. The system may operate in a fail-safe way such that the devices defaults to a safe heart rate range if, for example, no respiratory input is received.

The fourth stage 1410 determines the duty cycle of respiration, hence the duration of the inspiration and expiration phases. The cardiac frequencies sought during the inspiratory phase ($f_{insp}$) and the expiratory phase ($f_{exp}$) are set in the fifth stage by the "high pulse level" and "low pulse level" respectively. The choice of an inspiratory of expiratory frequency depends on whether the threshold comparator 1408 determines that the signal is associated with the inspiration phase or the expiration phase.

The fifth stage 1412 is configured to provide the cardiac frequencies sought during the inspiratory phase ($f_{insp}$) and the expiratory phase ($f_{exp}$). Practically the "low pulse level" and "high pulse level" set the two current levels $I_{insp}$ and $I_{exp}$ in the square current profile output by the fourth stage 1410. An example of this square current profile is shown in FIGS. 8a, 9a, 10a. a timing of stimulus signals as a function of the signal indicative of respiration duty cycle in order to maintain a bias towards synchronization between the respiration period and an integer multiple of the stimulus signal periods. The system 1400 may enable a clinician to set a separate high and low pacing rate for each of the inspiration and exhalation phases of breathing by setting $I_{insp}$ and $I_{exp}$ levels. Respiration signals are detected from the patient's diaphragm movements and used to determine time windows of fast and slow pacing.

In the fifth stage 1410, the timings of electrical pacing signals are determined based on the desired pacing rates (inspiratory, $f_{insp}$/expiratory, $f_{exp}$) modified by the bias to synchronization to the respiratory rate and duty cycle. These "natural" cardiac frequencies are modified by the interaction with the respiratory period and duty cycle, as explained above with reference to FIG. 3. In this example, a spiking neuron 1412 is used as a non-linear oscillator in order to generate these timings. The inspiratory and expiratory frequencies are set by the two levels of the rectangular current profile injected into 1412. Central Pattern Generator (CPG) technology may be used to implement the spiking neuron. An example implementation of a neuronal oscillator is discussed above with reference to FIG. 15.

In some examples, the entire chain of stages in the signal processing unit may be provided by analogue electronics. Advantages of analogue implementations over digital implementations include the possibility to reduce circuit complexity, reduce power consumption and the ability to handle analogue input directly without analogue to digital conversion. Analogue pulses generated within the analogue chain may also result in naturally-shaped signals, which may assist with interaction with the subject.

In digital implementations, the operating frequency may be kept at less than 10 kHz, or less than 1 kHz, in order to reduce power consumption. Digital implementations may also provide an operational log in order to enable system performance to be monitored.

A further variable gain amplifier 1414, or lead drive circuit, is provided to generate pacing electrical signals and provide the pacing electrical signals at a pacing output. In this example, the variable gain output 1414 provides the functionality of the stimulus generator described previously with reference to FIG. 1.

Various aspects of implementation of a cardiac pacing device that implements the previously described method is described below with reference to FIGS. 16 to 22. Various techniques may be employed to selectively suppress pacing artefacts from contaminating the respiratory input and allow a clean respiration signal to be obtained (faithfully showing the inhalation and exhalation phases without the ECG). Such techniques include:
    use of a pilot tone to determine the time delay offset of parasitic (e.g. ECG) sources;
    output isolation;
    use of a low peak demand output stage; and
    pacing stimulus muting (or blanking).
    Implementation of these concepts is discussed below.

In some examples, a pilot tone may be fed to the one or more pacing electrodes, at a level and frequency outside the range which has a substantial effect on the heart, allowing it to be used to set the paths for optimum performance. The dynamic and periodic resetting of the optimal path equalisation may be advantageous as paths are likely to change as animals move and stretch.

Cancellation of this 'Common Mode' signal, whilst maintaining sensitivity to lower level differential dEMG signals may benefit from a method of compensating for (nullifying) different effective path lengths between heart stimulation point and each of the dEMG sensor electrodes. The aim being to make unwanted signals, such as ECG, arriving at each of the differential EMG sensor electrodes at different times, thereby minimising the amplification effect of high differential gain (required to amplify the wanted differential signal) and allowing rejection of the unwanted Common Mode signal within the limits of Common Mode Rejection capability of the amplifiers.

Figure 16:
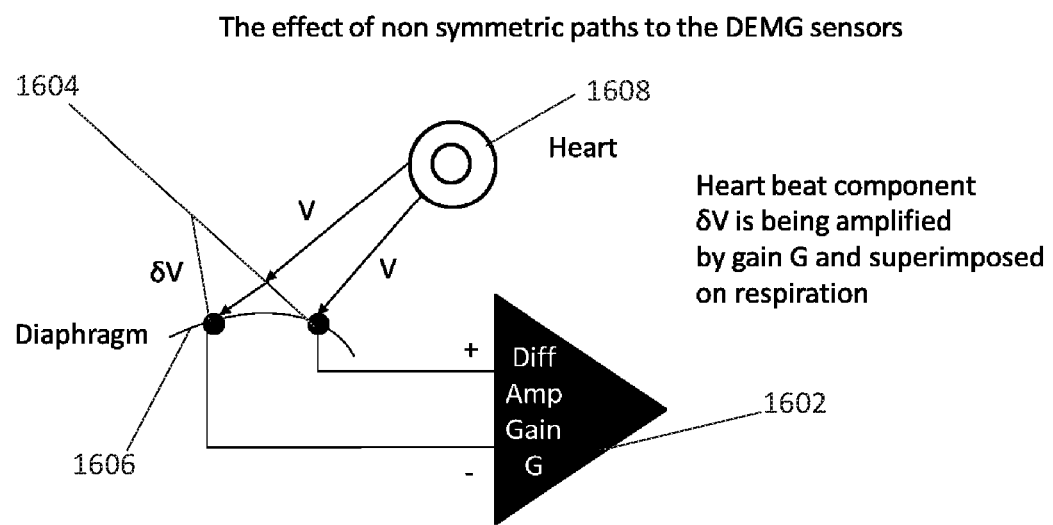
FIG. 16 illustrates a differential mode amplifier with a gain and delay offset cancellation.

FIG. 16 illustrates a differential mode amplifier 1602 with a gain (G) and delay offset cancellation. The latter is used in order to compensate for the effect of asymmetric paths to the dEMG sensors 1604. High common mode rejection devices and differential inputs may be used to improve the signal-to-noise ratio of the respiration signal. The dEMG sensors 1604 are provided on a diaphragm 1606 of a subject and are offset from a heart of the subject 1608. There is therefore a different path length between the heart 1608 and the respective dEMG sensors 1604. The dEMG leads 1604 on the diaphragm pick two signals: the respiratory signal+the ECG signal coming from the heart. The provision of the differential mode amplifier with delay offset cancellation enables the heartbeat component δV to be filtered out from the input so that the one signal amplified by gain (G) is the respiration signal only (EMG signal). That is, the dEMG leads cancels the ECG signal and only the respiratory signal from the diaphragm is amplified.

FIG. 17 illustrates an example in which the dEMG sensors 1704 are provided on a diaphragm 1706 of a subject and are equally spaced from a heart of the subject 1708. There is therefore the same path length between the heart 1708 and the respective dEMG sensors 1704. The same signal is therefore obtained by the respective dEMG sensors 1704. The differential reading dEMG=Lead A−Lead B will cancel out ECG signal and only contains the respiratory signal from the diaphragm. In this ideal situation, no delay offset would need be applied by the amplifier of FIG. 16.

FIG. 18 illustrates an example in which the dEMG sensors 1804 are provided on a diaphragm 1806 of a subject and are offset with respect to a heart of the subject 1808. There is therefore a different path length between the heart 1808 and the respective dEMG sensors 1804. The sensor closest to the heart receives a stronger signal than, and at an earlier time from, the signal obtained by the further sensor. In this case the differential reading dEMG will contain a residual artefact arising from the ECG. It is in this case that the delay offset of the amplifier of FIG. 16 will need adjusting to cancel out the ECG contribution to the dEMG reading Optical isolation may be used to avoid minute unwanted signals becoming superimposed on the power supply and ground signals from the pacing output stages (swinging at several volts) being passed onwards through common power supply connections to the high gain amplifiers of the respiration detection signals. The separation using one or more opto-isolators between the spiking neuron 1412 and the further variable gain amplifier 1414 breaks a Galvanic connection giving two isolated power supply regions, reducing unwanted coupling via the power supplies. Alternative techniques such as radio frequency isolation may also be used.

Figure 19:
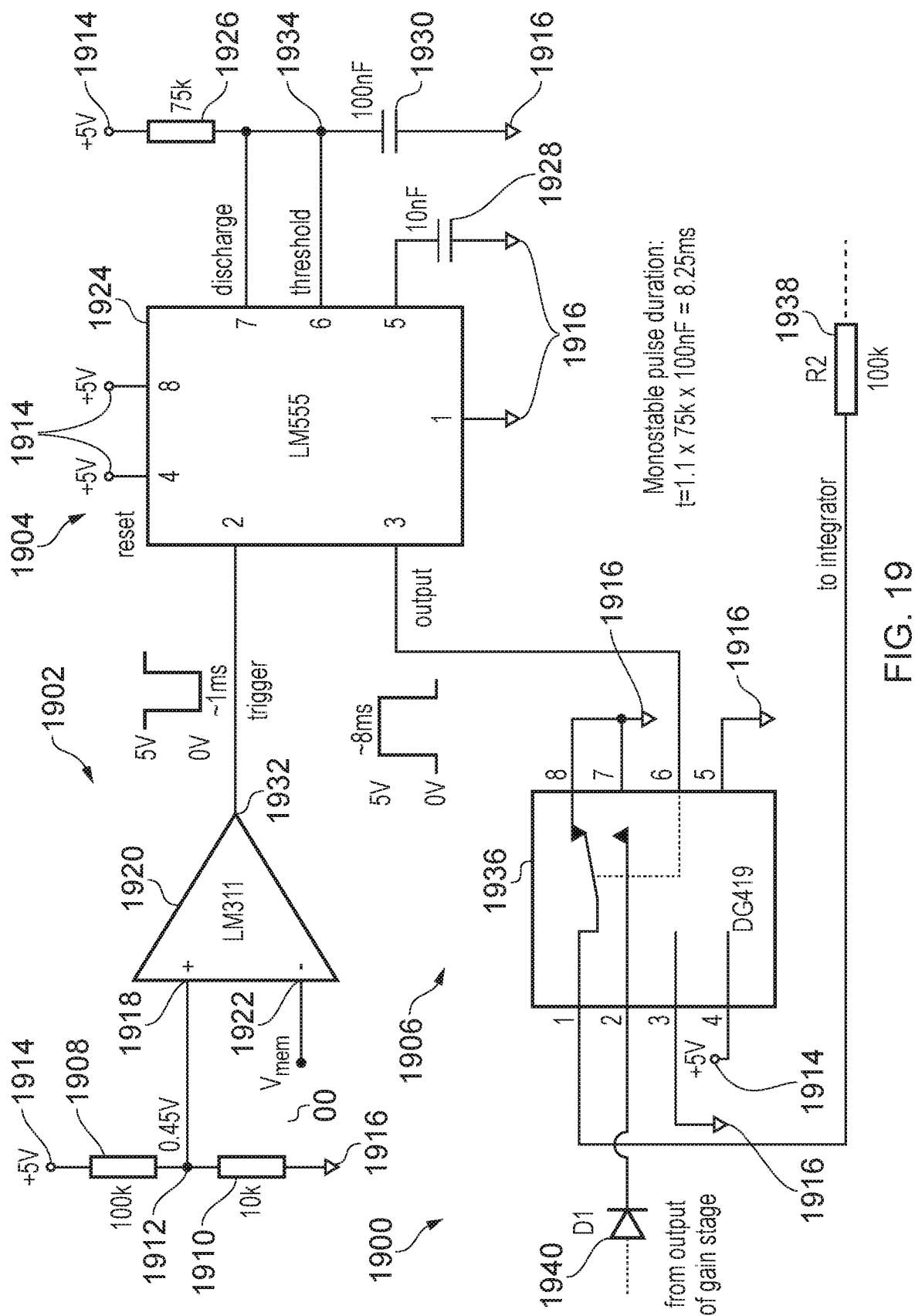
FIG. 19 illustrates an example EMG blanking circuit.

An alternative and more robust strategy to eliminate spurious ECG in the dEMG signal is to blank the dEMG input during the relatively short time interval (~10 ms) during which the pacemaker (FIG. 14) stimulates the heart. This blanking circuit is inserted between the rectification (1404) and filtering stages (1406) in FIG. 14. FIG. 19 illustrates an example EMG blanking circuit 1900 comprising a comparator module 1902, a timer module 1904 and a switching module 1906, which may be inserted between the rectification unit 1404 and filter 1406 in FIG. 14.

In this example, the timer module 1904 comprises a potential divider having a first resistor 1908 connected in series with a second resistor 1910 at a node 1912 between a voltage source 1914 and ground 1916. In this example, the voltage source 1914 is at +5V, the first resistor 1908 has a value of 190 kΩ and the second resistor 1910 has a value of 10 kΩ so that the voltage at the node 1912 is 0.45 V. The node 1912 is connected to a non-inverting input 1918 of an operational amplifier 1920. In this example, the operational amplifier 1920 is provided by LM 311. The inverting input 1922 of the operational amplifier 1920 provides the input to the blanking circuit 1900.

The timing module 1904 comprises a LM 555 integrated circuit 1924, a third resistor 1926, a first capacitor 1928 and a second capacitor 1930. The LM 555 integrated circuit 1924 has 8 terminals numbered in the conventional manner. Terminal 1 is connected to ground 1916. Terminal 2 is connected to an output 1932 of the operational amplifier 1920. Terminal 3 provides an output of the LM 555 integrated circuit 1924. Terminals 4 and 8 are connected to the voltage supply 1914. Terminal 5 is coupled to ground 1916 via the second capacitor 1928. The second capacitor 1928 is a decoupling capacitor and has a value of 10 nF. The third resistor 1926 and first capacitor 1930 are provided in series between the voltage source 1914 and ground 1916 and coupled together at a node 1934. This combination gives the RC time constant that sets the ~8 ms duration of the output pulse. The node 1934 is connected to terminals 6 and 7 of the LM 555 integrated circuit 1924. The first capacitor 1930 has a value of 100 nF. In this configuration, the timer module 1904 provides an output pulse with a high logic level at the third terminal in response to receiving a trigger signal with a low logic level at the second terminal. The component value selected in this example provide an 8.2 millisecond long blanking window following the depolarization of the spiking neuron $V_{mem}$>0.45V in 1902. This $V_{mem}$ is the membrane voltage output by the spiking neuron (1412) in FIG. 14, which gives the heart stimulation signal (after passing through amplifier stage 1414).

The switching module comprises a DG 419 integrated circuit 1936. The DG 419 integrated circuit 1936 has 8 terminals which are labelled in the conventional manner. During the 8.2 ms blanking window, terminal 1 is disconnected from terminal 2 and grounded via terminal 8. Terminal 1 may be connected to the filter input 1406 in FIG. 14 and terminal 2 may be connected to the rectification output 1404 in FIG. 14. Terminal 1 may provide the eventual output of the circuit 1900 for supplying the filtering circuit 1406 of FIG. 14. Resistor 1938 in FIG. 19 may be the first component of this filter circuit 1406. The second terminal receives the output of the rectification stage (1404 in FIG. 14). The third, fifth, seventh and eighth terminals are coupled to ground 1916. The fourth terminal is coupled to the voltage source 1914. The sixth terminal of the DG 419 integrated circuit 1936 is connected to the third terminal of the LM 555 integrated circuit 1924. The input to the sixth terminal of the DG 419 integrated circuit 1936 controls whether the output to the filter at the first terminal is connected to the eighth terminal (ground 1916) or the second terminal (from the output of the rectification stage).

The muting circuit may be triggered on each pacing stimulus output $V_{mem}$ to decouple the input leads by grounding them over a time window including the pacing pulse and follow-up damped oscillations from biological tissue. The duration of the time window may be adjusted from 0-8 ms based on a trade-off between blanking large artefacts and erasing useful dEMG signals. There is also small but finite travel time of the pacing signal through the heart muscle allowing the blanking circuit to be triggered before the dEMG input receives spurious ECG feedback from the heart. The blanking window is relatively small (8 ms in this example) compared to the heart rate period (~1 s) and respiration period (~3 s). The use of the blanking circuit 1900 is also minimally invasive.

Figure 20:
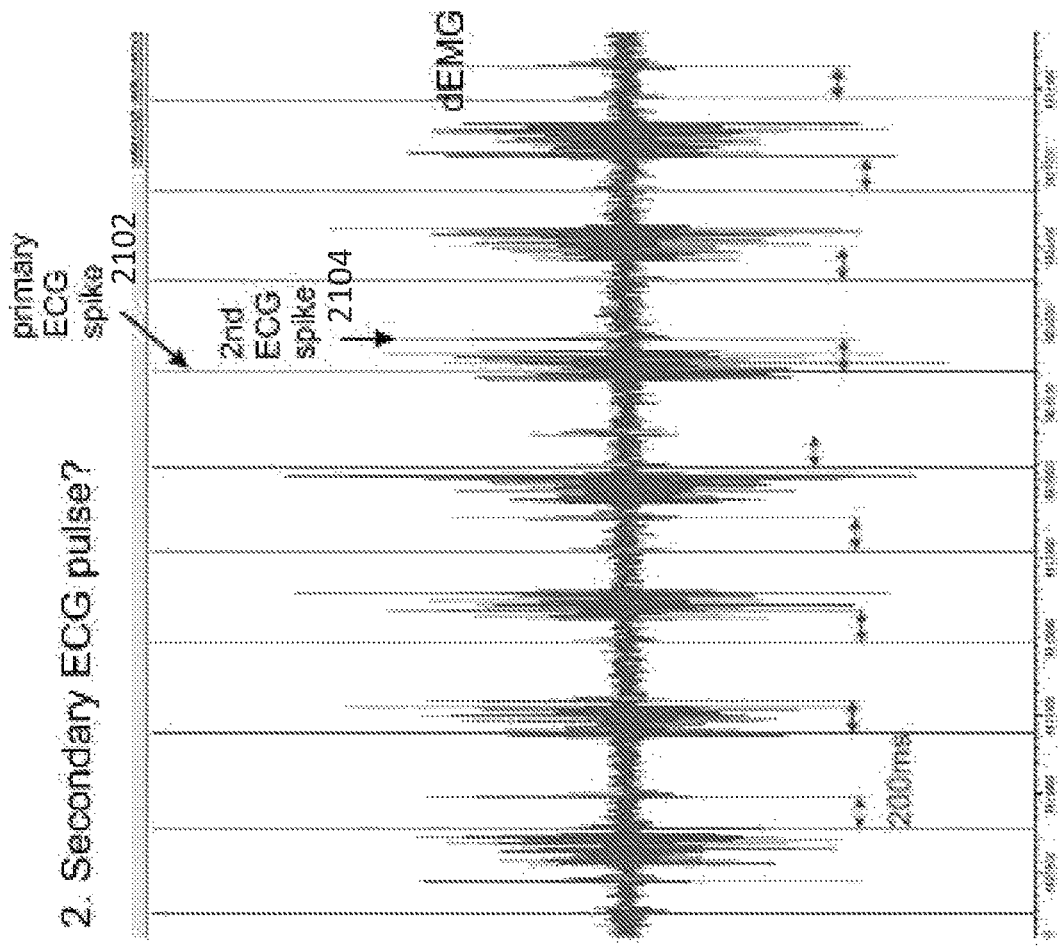
FIG. 20 illustrates a profile of an electrical stimulus pulse applied to a patient such as that received by the blanking circuit of FIG. 19.

FIG. 20 illustrates a profile of an electrical stimulus pulse 2002 (also labelled δV in FIG. 16 or dEMG in FIGS. 17 and 18) applied to a patient such as that received at the input of the comparator module of the blanking circuit of FIG. 19 and a corresponding dEMG signal 2003 obtained from a subject of the electrical stimulus pulse 2002. The dEMG signal 2003 comprises a primary pulse 2004 that coincides with the electrical stimulus pulse 2002, a secondary pulse 2006 reflected from patient tissue and a tertiary pulse 2008. The width of the blanking period (up to 25.2 ms) 2012 may be set based on a measured period (8.5 ms) 2010 between the primary pulse 2004 and the secondary pulse 2006, In this way, calibration of the blanking time window (<25 ms) to blank ECG-related pulses may be achieved.

Figure 21:
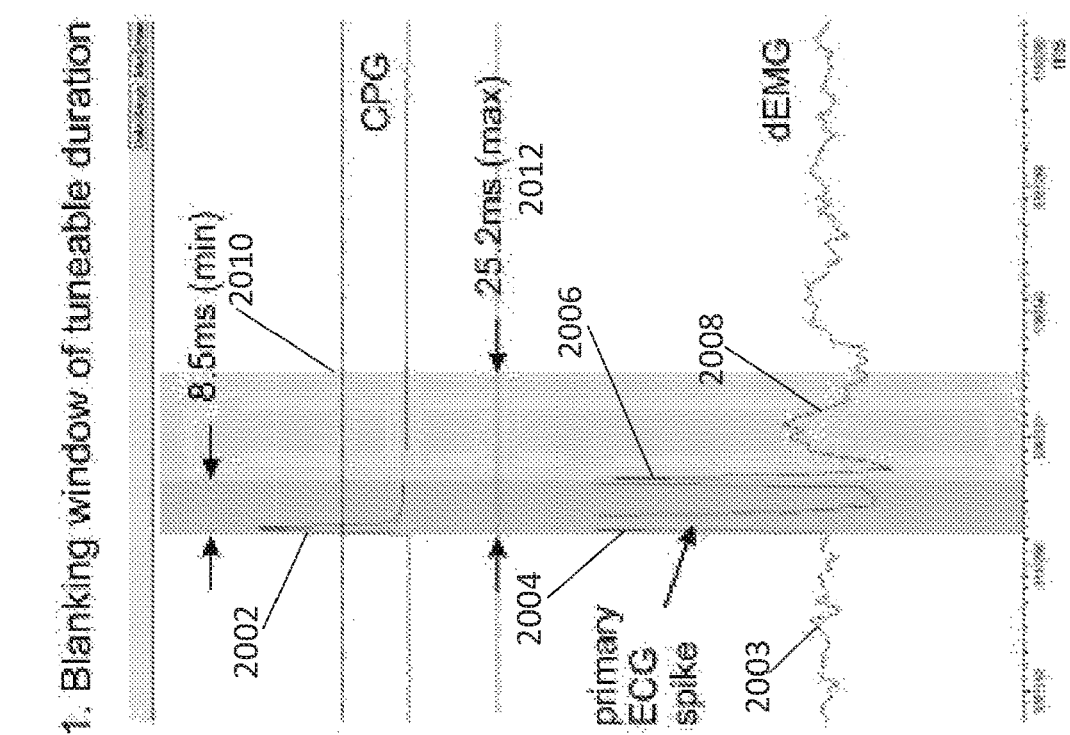
FIG. 21 Illustrates an ECG spike being a pulse of very large amplitude but very short duration relative to the breathing cycle.

FIG. 21 Illustrates the ECG spike is a pulse of very large amplitude but very short duration relative to the breathing cycle. This makes the blanking approach a viable non-invasive approach for compensating for the effects of pacing, FIGS. 22a to 22c illustrates example of recovered respiration envelopes (upper races) and corresponding dEMG signals (lower traces).

Figure 22A:
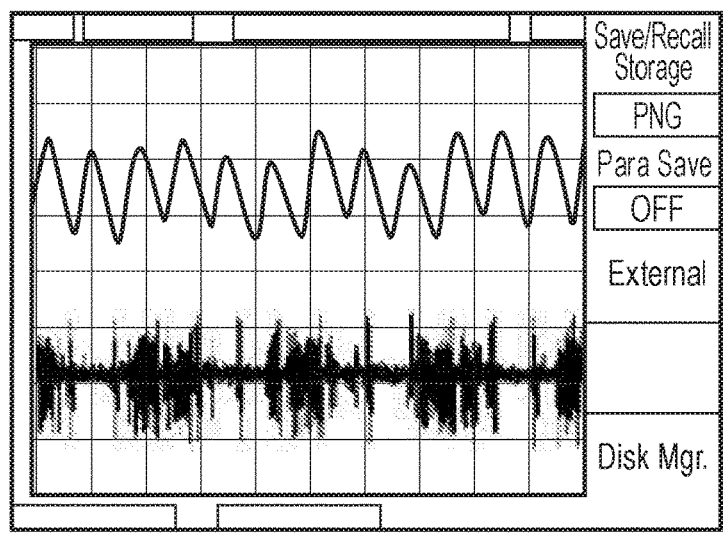
FIGS. 22a to 22c illustrates example of recovered respiration envelopes and corresponding dEMG signals.

FIG. 22a illustrates an extreme case in which the recovered respiration envelope, at test point TP2 in FIG. 14, (top trace) is distorted by no delay offset equalisation/nulling of differential paths and pacing artefact contamination makes the envelope unusable as a representation of breathing activity (envelope of bursts in lower trace.)

Figure 22B:
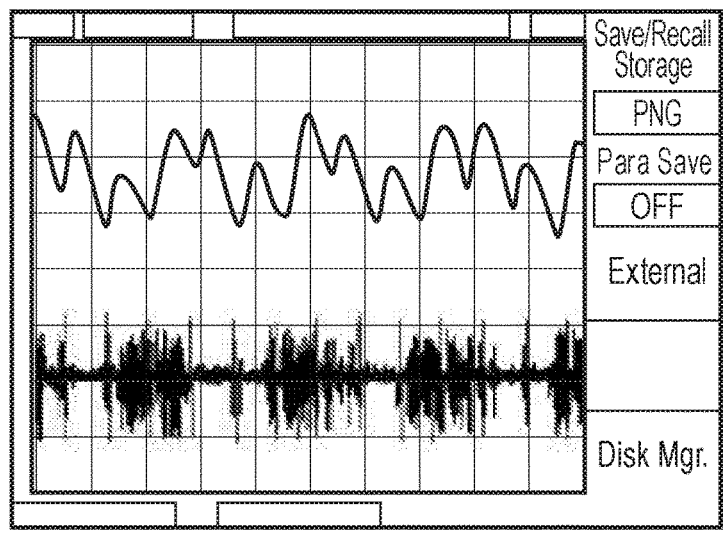

FIG. 22b illustrates similar signals to those in FIG. 22a but showing improvement of recovered respiration envelope as the path delay equalisation/null point is approached.

Figure 22C:
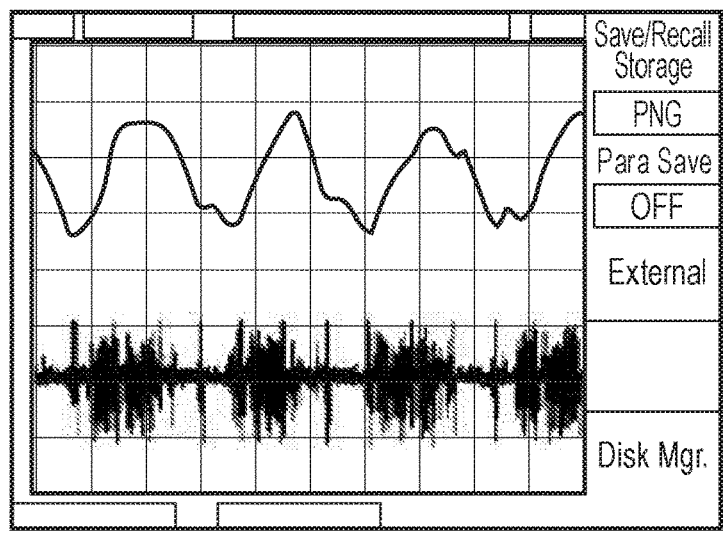

FIG. 22c illustrates an upper trace shows correct recovery of respiration envelope from low level dEMG signal showing filtering out of high frequency components and faithful envelope representation despite presence of pacing spikes as unwanted components in dEMG signal (visible as narrow spikes in lower trace.)

Similar results to FIG. 22c are obtained when using the blanking circuit. This approach was used in animal testing described below.

Figure 23A:
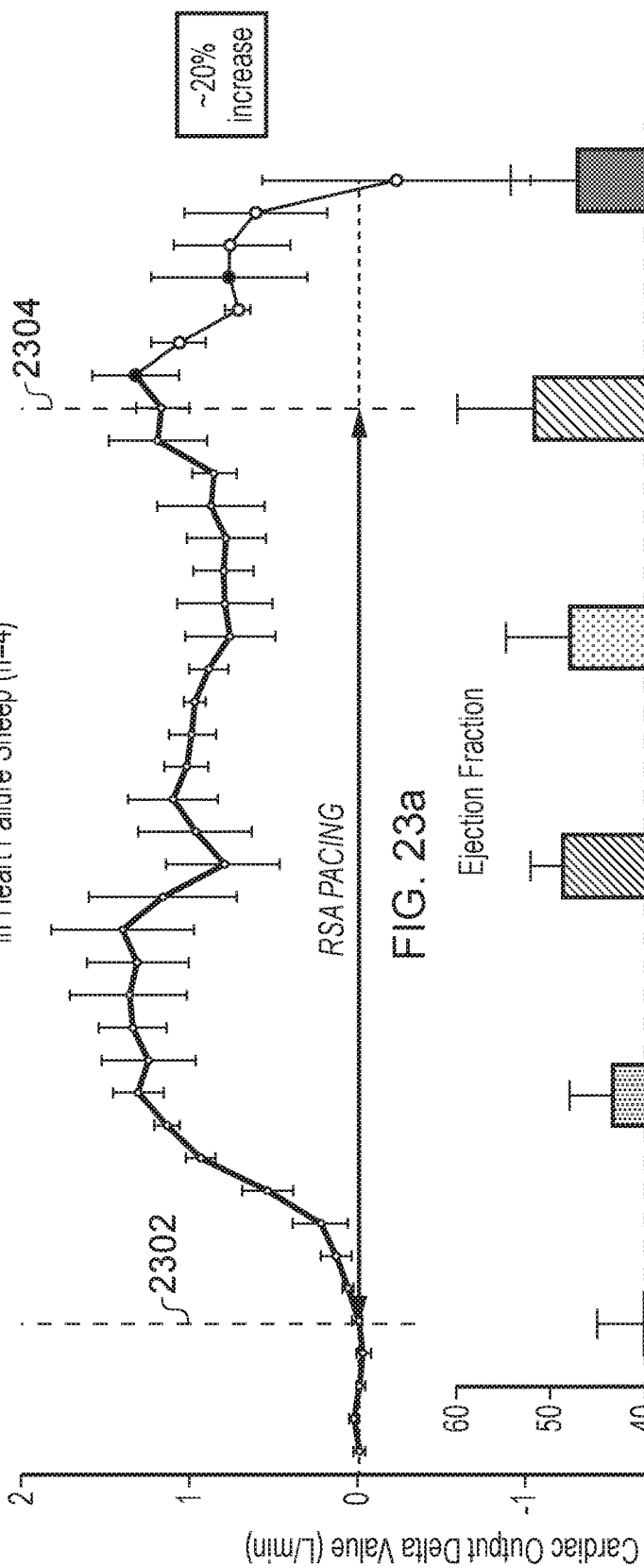
FIGS. 23a and 23b illustrate results from the application of RSA compensated pacing using the apparatus and method described previously in sheep.
Figure 23B:
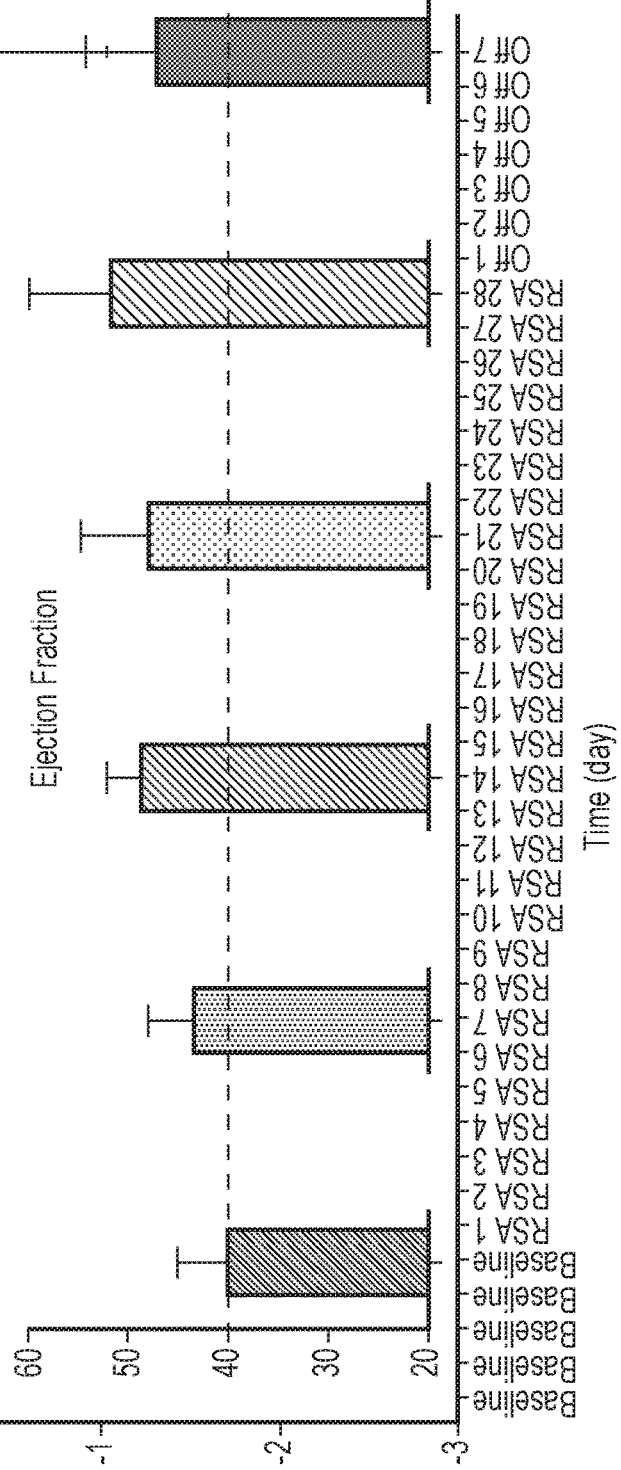

Data have been collected from animal testing which shows potential benefits of RSA pacing with an analogue CPG that exhibits non-linear behaviour. FIGS. 23a and 23b illustrate results from the application of RSA compensated pacing using the apparatus and method described previously in sheep.

The hypothesis that heart rate variability is present in health but lost in disease, and provides an early prognostic indicator for cardiovascular risk, was tested by the reinstatement of RSA in heart failure sheep (which have lost their heart rate variability) and observing the effect on cardiac pumping efficiency.

All sheep in this study received intra-coronary artery injections of microbeads under fluoroscopy visual guidance to induce heart failure, which was allowed to manifest chronically over 2-3 months. With ejection fractions reduced from 70-75% to 40-45%, animals were instrumented chronically to measure: blood flow from the ascending aorta (for cardiac output) and circumflex coronary arteries, arterial pressure, heart rate and dEMG in conscious sheep. Ejection fraction was measured using echocardiography. Sheep were either RSA or monotonically paced (control) for 4 weeks at around 15-20 beats/min above their intrinsic rate of 80 beats/min. RSA amplitude was set at 12 beats/min. This means that the pacing device with set up with $f_{insp}=112$ beats/min, $f_{exp}=100$ beats/min giving a RSA $(f_{insp}-f_{exp})/f_{exp}=12\%$. Additional sheep were not paced and acted as a time-based control.

FIG. 23a illustrates a profile of cardiac output delta values as a function of time, in days. After 2-3 days of RSA pacing, cardiac output increased (at marker 2302) steadily by 1-1.2 L/min over the next 4-5 days. This improved cardiac performance was maintained until RSA pacing was discontinued (marker 2304). In such circumstances, returning to RSA pacing again elevated cardiac output.

Figure 23C:
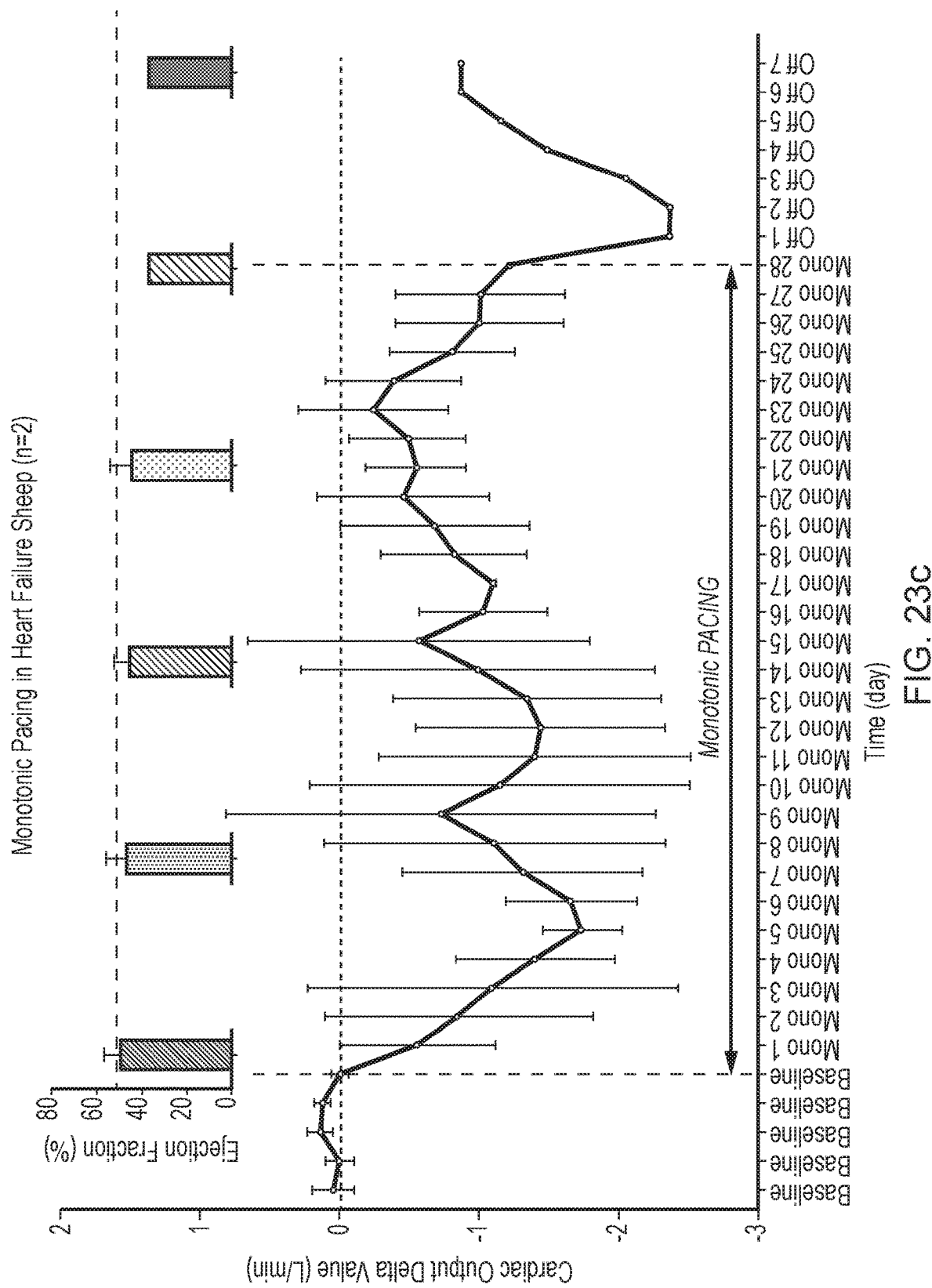
FIG. 23c illustrates results from the application of monotonic pacing in sheep.

FIG. 23b shows the ejection fraction of the sheep as a function of time during the trial. The ejection fraction increased by around 55% during RSA pacing. There was no obvious change in arterial pressure. After 4 weeks of RSA pacing, pacing was interrupted (2304). The elevated cardiac output was maintained for 2-3 days; after this time it reduced to or below pre-RSA pacing level. The latter suggests RSA pacing induced some memory or reverse-remodelling of the heart muscle. In contrast, as shown in FIG. 23c, the monotonically paced sheep (n=4) did show a decrease in cardiac output and the time controls a reduction (n=2).

RSA pacing has been shown to substantially improve cardiac pumping efficiency (via increases in cardiac output and ejection fraction) in sheep with heart failure. The magnitude of the effect is an unexpected increase in cardiac output of 18%.

The invention claimed is:

1. An apparatus for determining timing of electrical stimulus signals temporally modulated by a respiration signal, comprising:
   a first input stage configured to receive a first input signal indicative of respiration;
   a respiration analysis module configured to determine, from the first input signal, a signal indicative of instantaneous respiration duty cycle; and
   a synchronization module configured to:
   generate the timing of the electrical stimulus signals as a function of the signal indicative of instantaneous respiration duty cycle, and
   control synchronization of the timing of the electrical stimulus signals by determining discrete frequencies of synchronization that are based on combinations of inspiratory and expiratory frequencies in a respiration period such that a bias is maintained towards synchronization between the respiration period and an integer ratio of the periods between the electrical stimulus signals.

2. The apparatus of claim 1, in which the instantaneous respiration duty cycle has an inspiration phase and an expiration phase, the apparatus further including means for setting a parameter $(RSA=(f_{insp}-f_{exp})/f_{exp})$ determining a differential stimulus signal rate between the inspiration and expiration phases.

3. The apparatus of claim 1, in which each of the periods between the electrical stimulus signals within a single inspiration phase or expiration phase has a same target duration.

4. The apparatus of claim 1, in which the bias is maintained towards synchronization between the respiration period and the integer ratio of the periods between the electrical stimulus signals by setting a period for the periods between the electrical stimulus signals in an inspiration phase or an expiration phase.

5. The apparatus of claim 1, in which the synchronization module is configured such that a bias is maintained towards synchronization between an inspiration phase or an expiration phase of the respiration period and an integer multiple of the periods between the electrical stimulus signals.

6. The apparatus of claim 1, in which a different integer number of periods between the electrical stimulus signals is provided in an inspiration phase and an expiration phase.

7. The apparatus of claim 1 further including means for setting a strength of coupling factor to determine (i) a speed of synchronization between a non-linear oscillator and the instantaneous respiration duty cycle signal and/or (ii) a tolerance to frequency mismatch between the respiration period and one or more target heart beat intervals.

8. The apparatus of claim 1 in which the synchronization module modulates the timing of the electrical stimulus signals according to a non-linear function.

9. The apparatus of claim 8 in which the synchronization module comprises a neuronal oscillator.

10. The apparatus of claim 9 in which the synchronization module comprises a single neuronal oscillator.

11. The apparatus of claim 8 further including a non-linear oscillator configured to receive a second input indicative of a base frequency for a heart and the signal indicative of instantaneous respiration duty cycle, the non-linear oscillator synchronizing to the signal indicative of instantaneous respiration duty cycle.

12. The apparatus of claim 1, in which generating the timing of the electrical stimulus signals comprises modulating a base frequency for a heart.

13. The apparatus of claim 1, comprising an analogue electronic signal processing chain providing the respiration analysis module and the synchronization module.

14. The apparatus of claim 1, comprising a blanking module configured to provide a blanking period in the first input signal indicative of respiration based on i) the timing of the electrical stimulus signals or ii) based on detection of stimulus signal interference in the first input signal.

15. The apparatus of claim 1, in which the respiration analysis module is optically coupled to the synchronization module.

16. The apparatus of claim 15, in which the first input signal indicative of respiration is a dEMG signal, the respiration analysis module comprises an amplifier configured to amplify the first input signal, in which the synchronization module is galvanically isolated from the amplifier.

17. A system comprising:
a cardiac pacemaker device comprising the apparatus of claim 1;
one or more sensors coupled to the first input stage of the cardiac pacemaker device; and
pacing electrodes coupled to the cardiac pacemaker device and arranged to receive, from the cardiac pacemaker device, periodic electrical stimulus signals based on timing information determined by the cardiac pacemaker device.

18. A non-transitory computer-readable storage medium comprising computer program code configured to cause a processor to execute a method for determining timing of periodic electrical stimulus signals temporally modulated by a respiration signal, the method comprising:
receiving a first input signal indicative of respiration;
determining, from the first input signal, a signal indicative of instantaneous respiration duty cycle;
generating the timing of the periodic electrical stimulus signals as a function of the signal indicative of instantaneous respiration duty cycle; and
controlling synchronization of the timing of the electrical stimulus signals by determining discrete frequencies of synchronization that are based on combinations of inspiratory and expiratory frequencies in a respiration period such that a bias is maintained towards synchronization between a respiration period and an integer ratio of the periods between the periodic electrical stimulus signals.

* * * * *